(12) United States Patent
Margetis et al.

(10) Patent No.: US 10,653,201 B2
(45) Date of Patent: *May 19, 2020

(54) SYSTEM AND METHOD FOR HEAD AND SPINE IMMOBILIZATION AND PROTECTION

(71) Applicants: Konstantinos Margetis, New York, NY (US); Thomas Mroz, Cleveland, OH (US)

(72) Inventors: Konstantinos Margetis, New York, NY (US); Thomas Mroz, Cleveland, OH (US)

( * ) Notice: Subject to any disclaimer, the term of this patent is extended or adjusted under 35 U.S.C. 154(b) by 105 days.

This patent is subject to a terminal disclaimer.

(21) Appl. No.: 15/934,128

(22) Filed: Mar. 23, 2018

(65) Prior Publication Data

US 2018/0206579 A1 Jul. 26, 2018

Related U.S. Application Data

(63) Continuation of application No. 15/263,510, filed on Sep. 13, 2016, now Pat. No. 9,924,755, which is a
(Continued)

(51) Int. Cl.
*A42B 3/04* (2006.01)
*A61F 5/37* (2006.01)
(Continued)

(52) U.S. Cl.
CPC ............ *A42B 3/0473* (2013.01); *A42B 3/046* (2013.01); *A61F 5/3707* (2013.01); *F41H 1/04* (2013.01); *A41D 13/0531* (2013.01)

(58) Field of Classification Search
CPC . A63B 71/10; A63B 71/1291; A63B 2220/40; A63B 2220/53; A41D 13/0512;
(Continued)

(56) References Cited

U.S. PATENT DOCUMENTS

| 3,879,761 | A | * | 4/1975 | Bothwell | ............. | A42B 3/0473 |
| | | | | | | 2/415 |
| 4,396,797 | A | * | 8/1983 | Sakuragi | ................. | F16L 11/18 |
| | | | | | | 138/110 |

(Continued)

*Primary Examiner* — Jameson D Collier
*Assistant Examiner* — Jocelyn Bravo
(74) *Attorney, Agent, or Firm* — Kramer Levin Naftalis & Frankel LLP

(57) ABSTRACT

The present invention relates to a device that stabilizes and/or protects the head and spine from injuries. An immobilization device includes one or more pillars with multiple segments that protect the head and spine of a user. The pillars typically run along the part of the head and spine and pelvis that the device protects. A cable or wire runs through these segments in the pillars. By design, when the pillars of the invented system are not activated and the system is in normal use, the pillars are designed to be as flexible as possible and allow full physiologic motion of the protected body part. Activation of the system confers rigidity to the system and prevents or lessens harmful, non-physiologic motion of the body part intended to be protected. The present invention also encompasses a immobilization device with cables used to guide the deployment of rigid tubes to stabilize and protect the head of the user. The present invention further includes segments with flat guide protrusions for increased stability of the pillars. The immobilization device can further include rigid tubes that extent to receivers when they are activated, and which can also be used to stabilize and protect the head or neck of the user.

7 Claims, 29 Drawing Sheets

Related U.S. Application Data continuation-in-part of application No. 14/573,640, filed on Dec. 17, 2014, now Pat. No. 9,615,618.

(60) Provisional application No. 61/917,558, filed on Dec. 18, 2013.

(51) Int. Cl.
*F41H 1/04* (2006.01)
*A41D 13/05* (2006.01)

(58) Field of Classification Search
CPC .. A41D 13/0531; A42B 3/0473; A42B 3/046; A61F 4/3707; F41H 1/04
USPC .............. 2/6.6, 468, 410; 602/17, 18, 19
See application file for complete search history.

(56) References Cited

U.S. PATENT DOCUMENTS

| | | | |
|---|---|---|---|
| 4,589,407 A * | 5/1986 | Koledin | A61F 5/05883 128/869 |
| 5,287,562 A * | 2/1994 | Rush, III | A41D 13/018 2/413 |
| 5,371,905 A * | 12/1994 | Keim | A42B 3/0473 2/413 |
| 5,546,609 A * | 8/1996 | Rush, III | A63B 71/10 2/413 |
| 6,408,888 B1 * | 6/2002 | Baumer | F16G 13/16 138/120 |
| 7,849,525 B2 * | 12/2010 | Ghajar | A42B 3/046 2/410 |
| 8,448,669 B2 * | 5/2013 | Wen | B60T 11/046 138/119 |
| 8,497,427 B2 * | 7/2013 | Wen | F16C 1/26 174/102 R |
| 9,101,454 B2 * | 8/2015 | Duncan | A61F 5/05883 |
| 9,370,237 B2 * | 6/2016 | Hiemenz | A45F 3/04 |
| 9,492,306 B2 * | 11/2016 | Siegler | A42B 3/0473 |
| 9,586,125 B2 * | 3/2017 | McNeil | A63B 71/12 |
| 9,924,755 B2 * | 3/2018 | Margetis | A42B 3/0473 |
| 10,537,147 B1 * | 1/2020 | Ashline | A42B 3/08 |
| 2003/0088906 A1 * | 5/2003 | Baker | A42B 3/0473 2/416 |
| 2004/0255368 A1 * | 12/2004 | Baker | A42B 3/0473 2/410 |
| 2006/0150984 A1 * | 7/2006 | Ferguson | A61F 5/3707 128/846 |
| 2007/0186329 A1 * | 8/2007 | Baker | A42B 3/0473 2/410 |
| 2007/0245464 A1 * | 10/2007 | Baker | A42B 3/0473 2/411 |
| 2008/0256684 A1 * | 10/2008 | Ashline | A42B 3/0473 2/411 |
| 2009/0064396 A1 * | 3/2009 | Ghajar | A42B 3/0473 2/411 |
| 2012/0222197 A1 * | 9/2012 | Nagely | A42B 3/0473 2/410 |
| 2015/0245680 A1 * | 9/2015 | Partlo | A42B 3/046 2/411 |
| 2016/0058092 A1 * | 3/2016 | Aldino | A42B 3/046 |
| 2016/0157543 A1 * | 6/2016 | Huang | A42B 3/0473 2/411 |
| 2017/0006952 A1 * | 1/2017 | Staton | A42B 3/046 |
| 2017/0113115 A1 * | 4/2017 | Gilardo | A63B 69/0059 |
| 2017/0127747 A1 * | 5/2017 | Thalken | A42B 3/0473 |
| 2017/0150767 A1 * | 6/2017 | Wetzel | A63B 71/10 |
| 2017/0245576 A1 * | 8/2017 | Hetzler | A42B 3/0406 |
| 2017/0303623 A1 * | 10/2017 | Sicking | A42B 3/064 |
| 2018/0028091 A1 * | 2/2018 | Huang | A42B 3/0473 |
| 2018/0229070 A1 * | 8/2018 | McBride | A63B 21/4001 |
| 2019/0045871 A1 * | 2/2019 | Stade | A42B 3/145 |

* cited by examiner

SYSTEM AND METHOD FOR HEAD AND SPINE IMMOBILIZATION AND PROTECTION

CROSS-REFERENCE TO RELATED APPLICATIONS

This application is a continuation of U.S. patent application Ser. No. 15/263,510, filed on Sep. 13, 2016, which is a continuation-in-part of application Ser. No. 14/573,640, filed on Dec. 17, 2014 by inventors Konstantinos Margetis and Thomas Mroz, which application claims benefit and hereby incorporates by reference provisional application Ser. No. 61/917,558, entitled "System and Method for Head and Spine Immobilization and Protection," filed on Dec. 18, 2013 by inventor Konstantinos Margetis.

BACKGROUND

Spine and traumatic brain injuries cause significant morbidity and mortality due to events both in the civilian and military field. From a civilian perspective, extreme sporting enthusiasts are at risk for head and spinal injuries due to direct impacting or to non-physiologic, harmful extremes of motion. From a military perspective, spine injuries and traumatic brain injuries can occur as a result of explosions. Such blast injuries can be divided into four main categories:

Primary: Caused by the direct effect of blast overpressure on tissue of a victim. In some situations the blast will cause a differential acceleration of the head in relation to the body, because the body might be heavier (e.g. due to equipment carried) or because it might be protected (e.g. in armored vehicles' hatches or in trenches).

Secondary: Caused by fragments or flying objects (e.g. rubble, building fragments, and shrapnel) that strike people.

Tertiary: Occurs when blast victims fly through the air and strike other objects or the ground.

Quaternary: Includes smoke and debris inhalation, burns and any injury not previously described.

Currently, there is no head and spine protection device with widespread acceptance for protecting from spine and traumatic brain injuries when a user is subject to sudden, non-physiologic accelerations or decelerations, or extremes of bodily motion (e.g. spine range of motion, head range of motion), in the military or civilian arena. Some protective devices protect the spine but these devices are bulky, heavy and significantly reduce the range of motion of the cervical spine (e.g. systems based on rods). Other protective devices provide limited stabilization (e.g. air bags—also prone to puncture or might cause injury from sudden inflation) or significantly reduce the range of motion (e.g. collars worn by race car drivers that only allow limited head turning). Accordingly, there remains a need for a lightweight, reusable, mobile, and effective device that protects a user from spine and traumatic brain injuries in accidents without significantly restricting the motion of the user while in everyday use.

SUMMARY OF THE INVENTION

There are three primary fields of application for the described invention. First, to protect the spine, head and brain of a user from harmful forces that cause non-physiologic motion, including, acceleration or deceleration, and extremes of motion. Second, to protect the head and brain of a user from impacting objects, such as rocks, shrapnel or other debris. Third, to immobilize the head and neck of a user for comfort.

In some example embodiment, an immobilization device includes one or more pillars with multiple metallic (e.g. steel, titanium, or aluminum or metal alloys), or synthetic (e.g. carbon fiber, ceramics, polymer, viscoelastic, rubber, plastic) segments that protect the head and spine of a user. The pillars typically run along the part of the head and spine and pelvis that the device protects. A cable or wire runs through these segments in the pillars. As used herein, the terms cable or wire are used interchangeably. By design, when the pillars of the invented system are not activated and the system is in normal use, the pillars are designed to be as flexible as possible and allow full physiologic motion of the protected body part. Activation of the system confers rigidity to the system and prevents or lessens harmful, non-physiologic motion of the body part intended to be protected (e.g. head or various parts of the spine).

In some example embodiment, activation of the immobilization devices is accomplished by a mechanism to rapidly cause the flexible, inactivated pillars to become rigid. The segments within the pillars can have a variety of shapes and geometries. Such shapes include, but are not limited to, cylindrical, cuboid, triangular or cone, and combinations and variations of these shapes. The shape of the segments may be symmetric or asymmetric and be designed in such a way to allow preferential motion (e.g. more flexion and less extension). A hollow lumen runs the length of the segments in the elongated dimension through which a cable or wire can be placed. The segments are strung together one after another, similar to links of a necklace. In some embodiments, an articulation between adjacent segments will help maintain orientation of the individual segments relative to one another, during system activation and deactivation. In most applications, it is preferable for the segments to be durable, heat resistant, compact and lightweight. In some example embodiments, one end of the segments are convex and the other end concave. The convex and concave ends may be spherical, triangular, rectangular or other geometrical shape of various dimensions. Further, they may be asymmetric to confer more rigidity in the activated state. As such, when the segments are used in a pillar, each end of a segment articulates with the respective end of the adjacent segment (i.e. in the case of spherical terminal ends, the concave ends articulate with convex ones). In the example embodiments where a cable or wire runs through the lumen of the segments, the cable or wire and segments can be tightened causing the segments to contract together, locking the segments together and causing the pillar(s) to become rigid. The surface of the concave and convex surfaces may be smooth or textured, and may be coated with a special material or enamel designed to provide the optimal friction between the two articulating ends.

In some embodiments, system activation causes a sudden translation of the segments and/or cable(s). Such translation causes impaction of one segment onto its adjacent segment(s). The interlocking geometry, articulating surfaces of the segments, materials of the segments, tightening forces and other variables work in concert, then, to confer the desired rigidity to the system. This translation, and subsequent locking of the cable(s) or wire(s) and segments into the activated, rigid state, occur in the housing mechanism located in thoracic regions (e.g. vest), in the pelvic apparatus, or as part of an exoskeleton.

In some example embodiments when activation, or rigidity, of the system needs to be rapid a number of mechanisms can be employed to activate the system. These include, but are not limited to, a pyrotechnic, compressed gas, electric, magnetic, electromagnetic, hydraulic, and/or mechanical (e.g. spring or band mechanisms) devices. The example mechanisms can provide the necessary tightening force, thus conferring the desired stability to the head relative to the body and/or to various regions of the spine. In other example embodiments and applications where rapid activation is not necessary, activation and deactivation of the system is caused by manually tightening or loosening of the cable or wire and segments. Examples of how this can be done include, but are not limited to, an electric motor or a hand crank or a release cord.

Activation of this immobilization device can be triggered by various types of signaling between sensors, microprocessors, receivers, and other mechanisms built into a helmet (or other type of device on the head), a vest, pelvic harness, clothing, or vehicle. Examples of signaling include, but are not limited to, wires, fuses, radiofrequency, electric, or magnetic. Examples of the sensors include, but are not limited to light sensors, sound sensors, accelerometers or other motion sensor, pressure sensors (i.e. manometers), heat sensors and gyroscopes.

In some example embodiments, activation of one, or multiple, immobilization devices can be done remotely, or automatically, in a predetermined and secure manner. An example is a group of soldiers using the immobilization device that are, as a group, exposed to a blast. As one soldier's device closest to the blast is activated first, other devices worn by soldiers in what is deemed to be a dangerous perimeter to him/her can be activated, too, prior to the actual physical effects of the blast are experienced. In this case, the immobilization devices include wireless communication circuitry allowing communication between the immobilization devices.

In some example embodiments, the pillars connect to or span a portion or portions of the body intended to be protected. Connection to the head of the user will involve the pillars attaching in some way to a helmet, brace, band, or other device worn on the user's head. Such attachments can be anterior, lateral, or on the posterior aspect of the said device. There may be a single attachment point, or multiple attachment points. On the lower end of the user, the pillars attach either to a housing apparatus built into a vest in the upper or lower thoracic (anterior or posterior) region of the user and/or to a belt or specialized harness in the pelvic region. As mentioned the housing for the pillars may be built into a vest or may be a free standing apparatus, or harness, apart from a vest, worn by the user.

In some example embodiments, the system includes telescoping, pistoning, swiveling and/or rotating mechanism of the pillars to facilitate full, unimpeded motion of the head, neck, or mid and lower back when the device is not activated. This mechanism can be built into the helmet, vest or pelvic apparatus.

When the system is activated, the protected body parts are stabilized through the increase rigidity of the pillars. In the case of the head and neck protection, upon activation, the head and neck are stabilized and movement of the head and neck is prevented or minimized when the system is activated (i.e. when the pillar(s) are rigid). The pillars can confer different levels of rigidity depending of the circumstances and the intended application of the immobilization device. The pillars can be deactivated manually or automatically (e.g. after a predetermined time lapse or after harmful forces no longer detected). The rate of deactivation can be instantaneous or gradual.

The system may allow for multiple, sequential activation and deactivation cycles. The deactivation, again, can be manual or automatic. For example, automatic deactivation can be caused by a predetermined time lapse or when the dangerous forces or conditions causing the activation are no longer detected. In this way, for example, an extreme sporting individual or combat soldier or downhill skier using the device will be able to return to their activity during extreme or hazardous conditions.

In some embodiments, the pillars may have a protective sheath, sleeve, or covering, to prevent buildup of dirt, sediment, or other material or substance that could interfere with the desired function. The sheaths or sleeves composition can include materials including, but not limited to, plastic, cloth, metal, or silicone.

In some example embodiments, the immobilization system described herein allows the spine of the user to retain its normal range of motion, reducing any impediment on the user and allowing flexion, extension, lateral bending, and rotation of the neck or back of the user to be preserved. Some of these movements (e.g. flexion and extension of the neck) are associated with a coupled translational and/or rotational movement; therefore, in some example embodiments the design of the system (i.e. length of pillars, telescoping and/or pistoning and/or swiveling and/or rotating mechanism) will accommodate for full or nearly full range of motion for the user when the immobilization device is not activated. In some example embodiments, the system's design (convex and concave surfaces of the segments that comprise the pillars, surfaces with appropriate coefficient of friction, length of pillars) permit physiologic motion by virtue of intersegment motion when in the system is not activated (i.e. flexion, extension, rotation, and lateral bending, as well coupled motions).

In some example embodiments, the device allows for increased mobility by allowing the cranial end of a pillar to telescope, piston, swiveling, rotate and/or slide in special receptors in the superior, or cranial, attachment. In this example embodiment, the upper end of the pillar may be wedge shaped, or another shape. Below the wedge shaped end of the pillar are two sliding cylindrical or spherical rollers, which are normally in the free moving position. When the system activates, a sudden tightening force is applied to the cable or wire that is transmitted all the way up to its superior end. The sudden acceleration of the wedge shaped end will exert a force to the cylindrical rolls that its direction forms an angle to the tightening axis. This force will cause the outward movement of the cylindrical rolls and then the rolls will engage to the locking recesses inside the receptors. The engagement of the rolls to the locking recesses stabilizes the cranial end of the pillar in relation to the receptor.

In some example embodiments, the pillars will attach to the helmet. The lower ends of the pillars may telescope and/or piston and/or swivel and/or rotate within the vest housing apparatus. This will allow for the physiologic range of motion to be preserved by the user. Similarly, if the lower back spine is protected, then the upper or lowers ends of the pillars would be able to telescope and/or piston and/or swivel and/or rotate within an appropriately designed housing to allow for physiologic motion.

In some example embodiments, it is desirable at times (e.g. non-combat situations, non-performance situations) to not have the pillar attached to the helmet or to the pelvic harness. The helmet articulation site can be detached by the user and stowed on the shoulder strap portion of the user's vest. Similarly, the user can easily reattach the pillars to the helmet during necessary instances. The lower pillars can similarly be detached by the user from the pelvic harness and then stowed onto a portion of the vest. Similarly, the user can easily reattach the pillars to the harness during necessary instances.

In some example embodiments, the system will be able to detect the position of the protected body part and adjust the degree of activation, and thus tightening, accordingly. In this way, the system will prevent non-physiologic recoil of a body part during activation. For example, in the case of the system being used to protect the head and neck (i.e. cervical and upper thoracic spine), if the system is activated with the neck flexed, it will lock in that position or in a similar position. This will prevent sudden and possibly unwanted recoil of the head. This is an important part of the locking mechanism design. This "proprioceptive" property of the system (i.e. detection of body position prior to activation) allows the locking mechanism to tighten the pillars only to the appropriate degree. This locking mechanism is intrinsic to the housing apparatus, which can be built into a vest, pelvic apparatus, or can be made a component of an exoskeleton. Such rigidity of the system during activation can occur by several mechanisms. Examples include, but are not limited to: 1) the segments of the pillars forcibly pushed and locked into one another over the cable or wire; 2) translation of the cable or wire; or 3) both 1 and 2. By utilizing both the segments of the pillars forcibly pushed and locked into another over the cable or wire and translation of the cable or wire, rigidity to the system can occur with little to no recoil (i.e. of the head, for example).

In some embodiments, this device can be coupled with an exoskeleton system for use in the civilian or military contexts. In these cases, the housing apparatus for the pillars would be made intrinsic to the exoskeleton rather than into the vest or pelvic apparatus as described herein previously.

In some embodiments, the immobilization device uses the pillars and cable or cable system as a described above, but does not have the same tensioning and tightening mechanism. Instead, this embodiment relies on the shape and geometries of the segments and the cables or wires that comprise the pillars to prevent extremes of spinal motion and occipital, such as cervical motion (i.e. junction of head to spine). As described in previous embodiments, the segment geometry and materials, cable or wire, and the housing apparatus within the vest will be designed to withstand harmful forces that are known to occur in military activities (e.g. blast exposure, vehicle crashes) and in extreme sporting activities prior to system failure. In this way, the device will prevent non-physiologic extremes of the users body to occur, and hence, will prevent injury to the protected body part (e.g. spine).

In some embodiments, an immobilization device uses rigid tubes guided along cables or wires to provide support and stabilization. This example embodiment of an immobilization device includes conical receivers located on a helmet or pelvic harness. The conical receivers each have a cable or wire extending from them to a vest, which contains a housing apparatus. The cables or wires extending from the conical receivers attach to the housing apparatus within the vest. The rigid tubes can be retracted into the housing apparatus when the embodiment of the immobilization device is in the inactive state. However, the immobilization device can be activated based on the detection of an event such as an explosion, vehicle crash, or other rapid acceleration or deceleration. As a result of activation, the rigid tubes rapidly extend from the housing apparatus (in the thoracic region), guided by cables or wires extending from the canonical receivers and to the helmet or pelvic harness. The rigid tubes would mate with the conical receiver and provide rigidity to the system. In some embodiments, a housing apparatus for the rigid tubes is incorporated into the helmet of the immobilization device, instead of the vest, and when activated the rigid tubes extend inferiorly along the cable or wire to mate with the conical receivers that are on or within a vest. This rigid tube and conical receiver system can be activated based on the detection of events as describe above for the other embodiments of the immobilization device.

Example Applications

Some example embodiments of the immobilization system describe can used to prevent injury to airplane pilots. For example, ejection from a cockpit exerts significant vertical acceleration forces on fighter pilots, and shear forces resultant from the ejection at high velocity. A current trend is to incorporate additional helmet mounted systems, such as helmet-mounted displays; this trend increases the weight of the helmet and the forces exerted to the cervical spine during ejection. The proposed system can be used in this application and it can provide cervical spine protection during the fighter pilot ejection. In addition to the ejection forces, the fighter pilots are also subjected to high acceleration forces during air fights. The system can be used in this application and protect the head, neck and spine of the pilots when an excessive range of motion is detected. A different activating mechanism may be used in this application, because a repetitive activation will be needed, while the need for a very short activation time is not as essential as in other applications. The immobilization system can also protect airplane or helicopter crew and passengers from crash landings.

An additional example embodiment of the immobilization system protects combat soldiers from arms fire and explosions. For example, when a bullet strikes the head of a person there are two mechanisms that can cause brain damage. Firstly, it is the direct injury by the penetration of the skull. However, since lighter and stronger materials are being developed, a protective plate that can resist the penetration of a bullet is now feasible. If the plate stops the penetration of the skull by a bullet, there is a second mechanism that can cause brain damage through the sudden acceleration of the head caused by the bullet. The incoming bullet has marked momentum and kinetic injury and once it strikes the helmet, according to the law of conservation of momentum, a sudden acceleration to the head will ensue. The terminal velocity of the head/plate relates to the mass. The proposed application will connect the helmet/head to the rest of the body, significantly increasing the mass that the bullet hits and therefore decreasing the terminal velocity and the acceleration forces transmitted to the brain. The gyroscope, or similar mechanical, electric, and/or magnetic sensor will cause activation and, in turn, will stabilize not only cervical spine, but also the head. The activation can be achieved either by an accelerometer sensor or a direct activation by the incoming bullet of a coiled detonation cord placed in front of the head protective plate.

Another important combat application pertains to exposure to blasts. Spinal injuries and traumatic brain injuries can result from either sudden acceleration (i.e. due to blast pressure wave), or from sudden deceleration (e.g. vehicle in collision) of the head or body resulting in brain and/or spinal cord and/or spinal column and/or nerve injury. The system is designed to activate with the described mechanism under such situations created by blasts, and to protect the user of this device from injury. The immobilization system can be used in these applications to protect the individual from spine injuries during impact, while allowing for a full range of motion of the spine at the inactivated state of the device. In certain example embodiments, the immobilization system will interface with the vehicle that has an accelerometer or other device to detect the acceleration/deceleration/hazardous changes to angular velocity, yaw and/or pitch caused by the blast wave or vehicular accident. The accelerometer or other motion, position or impact sensor sends a signal to the immobilization system(s) worn by the user(s) to activate. This allows for an early activation of the immobilization system, prior to the acceleration/deceleration effects reaching the user of the immobilization device. Some newer military vehicle concepts describe the use of rapid evasive maneuvers from the vehicle in order to avoid incoming fire. The immobilization system could prevent injuries during these evasive maneuvers. The activation of the immobilization system in this embodiment can be gradual to mitigate the acceleration forces transmitted to the brain and spine.

In another example embodiment, the immobilization system can provide head support for travelers in the sitting position. Again, since rapid activation is not necessary a manual tightening system can be utilized. Since the anticipated forces are small, the system can be built from cheaper material with less stiffness.

The immobilization device can have a caudal extension, which can be a few centimeters long, extending down approximately to the tip of the coccyx, rigid and connected to the caudal end of the pillars and the belt. The caudal extension can be connected to a receptor in the seat in the vehicle the user is traveling in and in this case the immobilization system may offer an immobilization of the person to the seat, and may negate the need for safety belts. In such a case, the person would have greater mobility compared with using the safety belt, while enjoying a greater degree of protection when the immobilization system is activated. The caudal extension can have a "T" configuration, but a person of ordinary skill in the art would understand that a number of geometries are possible based on the anticipated application. For example, if the caudal extension is intended to be inserted in a receptor in a seat, the caudal extension can have a tongue shape commonly used with seat belts to be inserted into a buckle.

In a further example embodiment, the immobilization system can be used by those skiing, snowboarding, rock climbing or other activities, such as "extreme sports", putting the user at risk of sudden accelerations/decelerations or harmful motion or impact through falling unsafe distances, or by being hit by falling debris.

Another method of protection conferred by this invention is prevention of injury from axial loading. A person of ordinary skill in the art could understand that all injuries to the spine and brain do not occur by strict angular or rotational motion, and indeed, some injuries can occur by direct axial loading. Examples include falling onto one's head, falling from a height onto the buttocks, or sitting in a military vehicle while an explosion occurs under that vehicle. Such forces can cause catastrophic, permanent injury to the brain, spinal column, spinal cord and nerves. The device is designed to act as an exoskeleton or external brace by channeling the axial forces to the device and away from the person's body. This external splint will prevent brain and spinal injury.

BRIEF DESCRIPTION OF THE DRAWINGS

A better understanding of the present invention can be obtained from the following detailed description in conjunction with the following drawings, in which:

FIGS. 22A, 22B, 22C depict example embodiments of conical receivers with different geometries.

DETAILED DESCRIPTION OF THE PRESENT INVENTION

Figure 1:
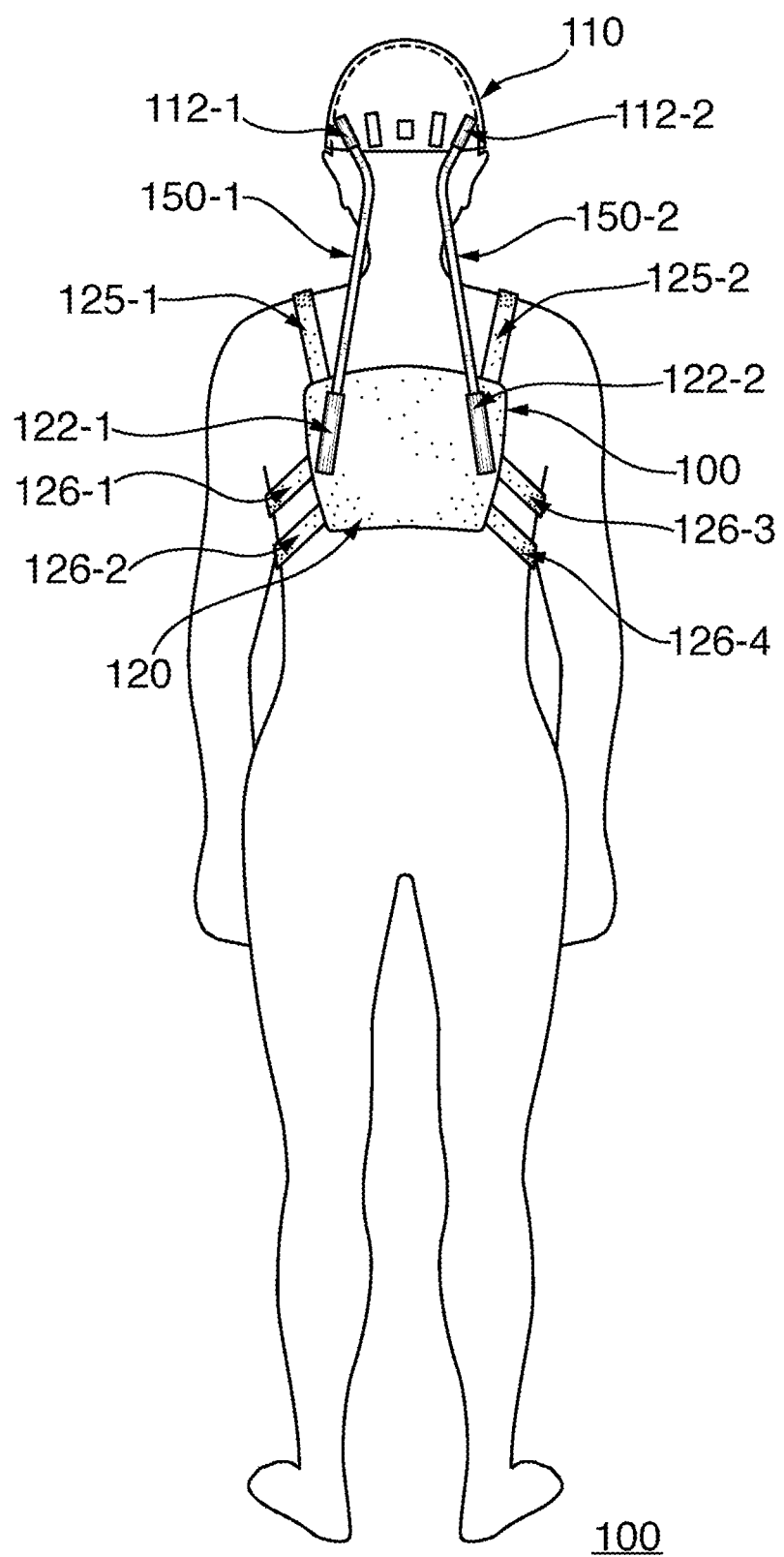
FIG. 1 depicts an example embodiment of an immobilization device with a vest.

FIG. 1 depicts an example embodiment of an immobilization device 100. The immobilization device 100 includes a helmet 110, a vest 120 and pillars 150-1 and 150-2. The helmet 110 includes helmet attachment points 112-1 and 112-2. The vest 120 includes attachment points 122-1 and 122-2, shoulder straps 125-1 and 125-2, and chest straps 126-1, 126-2, 126-3 and 126-4. The helmet 110 attaches to the vest 120 with pillars 150-1 and 150-2.

The immobilization device 100 is preferably made of lightweight materials, such as lightweight metals, fiberglass, composites or plastics. The pillars 150-1 and 150-2 attach to the helmet 110 at helmet attachment points 112-1 and 112-2, respectively. The pillars 150-1 and 150-2 extend from the helmet 110 and connect to the vest 120 at the vest attachment points 122-1 and 122-2. In the preferred embodiment, the vest 120 will be at or below the thoracic spine to increase the effectiveness of the immobilization device 100, although this is not necessary. The helmet 110 and vest 120 can be specially designed as part of the immobilization device 100, or in some example embodiments, can be an existing helmet and vest retrofitted with attachment points to connect to the pillars 150-1 and 150-2. For example, the helmet and vests used in the military can be retrofitted to be used as the helmet 110 and vest 120. In some example embodiments, the helmet 110 can be an existing helmet (e.g. motorcycle rider, fighter pilot, combat). The vest 120 can be an existing harness, vest or a new design specifically for this device. Preferably, the vest 120 has a wide rigid surface that disseminates forces to the surface of the thorax of the user. Preferably, the vest 120 should also attach circumferentially on the chest. In the example embodiment depicted in FIG. 1, the vest 120 includes chest straps 126-1, 126-2, 126-3 and 126-4 to secure the vest 120 to the user. The vest 120 further includes shoulder straps 125-1 and 125-2 to further secure the vest 120 to the user. The chest straps 126-1, 126-2, 126-3 and 126-4 and shoulder straps 125-1 and 125-2 may be of any material known and convenient and can be secured and/or tightened to the user via conventional means such as latches, buckles, or hook-and-loop fastener depending on the application.

The pillars 150-1 and 150-2 are flexible under normal conditions, referred to as the "inactivated" state for the pillars. The pillars 150-1 and 150-2 can also be in an "activated" state, where the pillars become rigid by a rapid tightening of an internal cable or wire that stabilizes multiple segments that collectively form the pillars 150-1 and 150-2. The segments can have a variety of shapes, have a lumen and are preferably durable to large forces or heat and made of a strong and lightweight material. In some example embodiments, one end of the segment is convex and the other end of the segment is concave. Each end of a segment articulates with the respective end of the adjacent segment (i.e. concave ends articulate with convex ones). Preferably, an inelastic cable or wire of sufficient strength properties runs in the lumen of the segments lumen. When the immobilization device 100 is in activated state, the pillars 150-1 and 150-2 become rigid as interlocking segments key into each other as the cable or wire is tightened or the segments are tightened together through a locking mechanism pushing the first segment in the chain forward. In some example embodiments and applications, particularly when immobilization is required as rapidly as possible, a pyrotechnic, compressed gas, magnetic, and/or electric mechanism or other mechanism known and convenient provides the necessary tightening force. The pyrotechnic, compressed gas, magnetic, and/or electric mechanism, in turn, activates a global device tightening and locking mechanism that confers rigidity to the head and upper spine through the helmet 110 and vest 120. In some example embodiments, the tightening of the cable or wire can be performed through the use of an electric motor or spring system embedded in the helmet 110 and/or vest 120. In other example embodiments, one segment will be shifted towards the other segments causing all the segments to compress together. In this example embodiment, the segment can be shifted with a spring, a compressed gas or explosives, or other mechanism capable of generating the desire force. The segment will then be locked in place in the shifted position. Example of the segments able to be used in immobilization device 100 can be seen in references to FIGS. 3A, 3B and 4. Examples of the how the segments can be used to activate the pillars 150-1 and 150-2 in immobilization device 100 can be seen in reference to FIGS. 5A, 5B, 10A, 10B, 100, 13A, 13B, 14A, 14B, 15A, 15B, 16A, 16B, and 17. Examples of the locking mechanisms that can be used in pillars 150-1 and 150-2 can be seen in reference to FIGS. 6, 7, 8A and 8B.

The pillars 150-1 and 150-2 include an optional sleeve covering the segments, which can be of any flexible material known and convenient such as nylon, plastic, or fabric. The pillars 150-1 and 150-2 may be enclosed in a flexible sleeve to protect them from corrosion or wear, and help prevent binding with neighboring materials. In some example embodiments, the sleeve may be made of cloth, soft plastic, rubber, nylon, leather, any combination of these materials, or any other material known and convenient to a person of skill in the art.

While FIG. 1 depicts the immobilization device 100 with two pillars, a person of ordinary skill in the art would recognize that a different number of pillars could be used. For example, in some example embodiments a single pillar may be sufficient. While in additional example embodiments, three or more pillars may be used for increased support. The number and the exact shape of the pillars will depend on the specific application. In applications where the user will be in the upright position, two pillars that run along the spine on the back of the user may provide adequate protection. In applications where the user is seated, then the pillars might run on the front of his body as well. The diameter and the number of the pillars used, as well as their location will depend on the overall stabilization required for the specific application. Furthermore, the number of segments used in a pillar will vary on the application, the length of the pillar, and the length of the segments. Preferably, enough segments will be used that when the cable or wire running through them contracts and the device activates, the segments lock together, but when inactivated are spaced enough apart so the segments are able to articulate.

The helmet attachment points 112-1 and 112-2 may attach the pillars 150-1 and 150-2 to the helmet 110 by a plain fixed attachment. The harness attachment points 122-1 and 122-2 may attach the pillars 150-1 and 150-2 to the vest 120 by a plain cylindrical, hollow connector, by rigidly fixing one or more segments to the vest 120. In some example embodiments, to accommodate neck or back flexion and extension the immobilization device 100 includes a telescoping mechanism in the helmet 110 or vest 120, permitting a greater range of motion. For example, the telescoping mechanism allows a user a greater range of motion for looking up at the sky; bending forward to tie one's shoes. The telescoping mechanism acts as a sheath through which the pillars 150-1 and 150-2 pass. The telescoping mechanism is shown in greater detail in reference to FIG. 8. In some example embodiments, the telescoping, pistoning, swiveling and/or rotating mechanism are built into the system housing located in the vest 120.

The immobilization device 100 may be activated in several ways. In some example embodiments, the electrical system of an aircraft, car, tank or other transportation system couple to immobilization device 100. The immobilization device 100 can be coupled to the electric system of a transportation system in any way known and convenient, such as through a wired data port connection like USB or wirelessly through a connection like Wi-Fi or Blue Tooth. In these cases, the transportation system can communicate with the immobilization device 100 and indicate if activation is necessary or appropriate. The control system can also provide information on the strength required in activation, allowing for more or less rigidity in the pillars depending on the detected conditions. For example, if a pilot is required to eject from an aircraft, the control system could communicate to or with the immobilization system 100 to activate and thereby stabilize the user during turbulence, a crash or harmful or unpleasant forces. In some further example embodiments, an accelerometer and/or gyroscope may be embedded in the immobilization device 100. When a sudden acceleration, deceleration or change in orientation is detected the immobilization device 100 may be activated. The accelerometer and/or gyroscope can also provide information on the strength required in activation, or provide data to a processor in the immobilization device able to calculate the appropriate response, and allowing for more or less rigidity in the pillars depending on the detected conditions. In some alternative embodiments, a combination of accelerometer and gyroscope is used to detect acceleration and orientation changes indicating the immobilization device 100 should be activated. Furthermore, the immobilization device 100 may include a manual activation switch or button, allowing the wearer to activate the immobilization device 100.

In some example embodiments of the immobilization device, an accelerometer is located in the helmet or at the cranial end of pillars 150-1 or 150-2 to sense any sudden acceleration or deceleration of the head. Moreover, in applications where sudden acceleration or deceleration is anticipated first in the thoracic or lumbar spine, then one or more accelerometers can also be placed in these locations (E.g. in the vest 120). In some example embodiments, the immobilization device includes a processor able to read various acceleration inputs and determine if activation of the immobilization device 100 is necessary or appropriate. The immobilization device can include a processor for determining the correct response based on the various acceleration or orientation inputs. This information can also be stored for later use on memory included in the immobilization device 100 to later reconstruct a timeline of events, similar to a "black box" on a commercial airliner.

In additional example embodiments, if there is a need to limit the electronics contained within immobilization device 100, then a mechanical or an electrical activation mechanism can be used. A short flexible cord suspends a sphere of weight. The sphere is connected through the cord to a pin that holds a firing pin. The pin-firing pin assembly attaches to the body part (e.g. head), whose acceleration will activate the device. An acceleration of sufficient force to the protected body part moves the pin/firing pin. When the cord of the free hanging sphere comes under tension, then the cord will exert a pulling force on the pin that is holding the firing pin. The pin is pulled out and the firing pin will be released. The firing pin will either hit a detonation cord to activate the system or it will close an electrical circuit, causing an electrical activation of the system.

In some example embodiments of immobilization device 100, particularly versions intended to protect the head from the impact of a bullet, an extremely rapid activation is required and activation of the immobilization device 100 is achieved by placing a coiled lightweight detonation cord in the head protection plate. The incoming bullet activates the detonation cord before reaching the protection plate. The detonation cord transmits the activation to the main activation pyrotechnic or compressed air charge with a speed sufficient to protect the user.

In example embodiments of immobilization device 100, particularly embodiments intended for applications for motorcycle riders, the immobilization device 100 connects to the motorcycle, or water vehicle. In the event of the user falling, this cable is pulled out and activates the system. An additional option is to have the activation of the immobilization device 100 be transmitted from a vehicle and/or computer or electrical system of the vehicle in which the user is riding. This activation can be triggered by electronic accelerometer attached to the vehicle that is designed to detect abnormal changes in direction or deceleration, or abnormal changes in direction (i.e. yaw, pitch, or roll). In the event of a collision or explosion that results in a sudden abnormal increase in yaw, pitch or roll of the vehicle, the immobilization device 100 will be activated to protect the user(s) in the vehicle. In further example embodiments, additional sensors may be used to detect changes in air pressure indicative of an explosion and required activation of the immobilization device 100.

The number of pillars used (one, two, three or more) in an immobilization device, and their spatial positioning can be variable and this will be predicated on the demands of the user and anticipated environmental situations (e.g. military combat, extreme sporting). The optimal positioning and number will confer maximal achievable resistance to motion in all planes.

Figure 2:
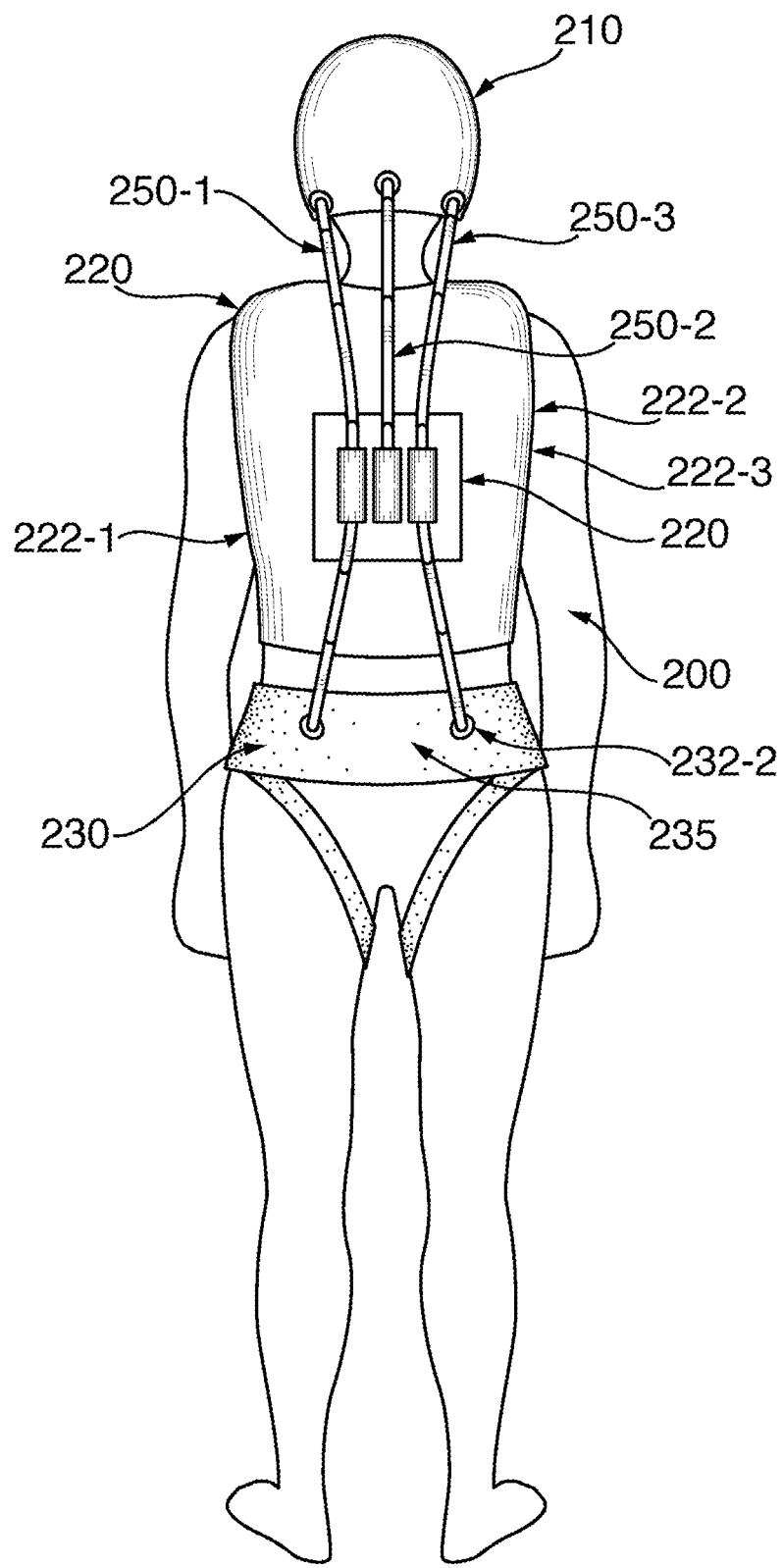
FIG. 2 depicts an example embodiment of an immobilization device with a vest and a belt.

FIG. 2 depicts an example embodiment of an immobilization device 200. The immobilization device 200 includes a helmet 210, a harness 220, a belt 230 and pillars 250-1, 250-2 and 250-3. The immobilization device 200 is similar in most respects to the immobilization device 200 depicted in FIG. 1, however the pillars 250-1 and 250-3 reach pelvis and attach to belt 230. Immobilization device 200 also includes a third pillar 250-2 that attaches to the harness 220. The pillar 250-2 can also extend to the harness in some embodiments, or that pillars 250-1 and 250-3 may attach only to the harness 220, while the pillar 250-2 attaches to the belt 230, depending on the requirements of the particular application. Examples of segments that can be used to activate the pillars 250-1 and 250-2 in immobilization device 200 can be seen in reference to FIGS. 5A, 5B, 10A, 10B, 100, 13A, 13B, 14A, 14B, 15A, 15B, 16A, 16B, and 17. Examples of the locking mechanisms that can be used in pillars 250-1 and 250-2 can be seen in reference to FIGS. 6, 7, 8A and 8B. The immobilization device 200 can be activated as described in reference to FIG. 1.

In some example embodiments, immobilization device 200 will have a caudal extension distal in the belt 230. An example of the caudal extension is described in greater detail in reference to FIG. 9. The attachment points to the vest 222-1, 222-2 and 222-3 might be hollow tubes that would allow the pillars to slide through. In this case the activation mechanisms are located in the helmet and/or belt. Alternatively, the attachment points 222-1, 222-2 and 222-3 might be anchoring points for the pillars and contain the activation mechanisms.

The immobilization device 200 includes a belt 230 that can have a rigid surface at the site of the pillars connection to disseminate force over a larger surface. Thigh straps can offer added stability to the system by creating an additional point of stabilization.

Figure 3A:
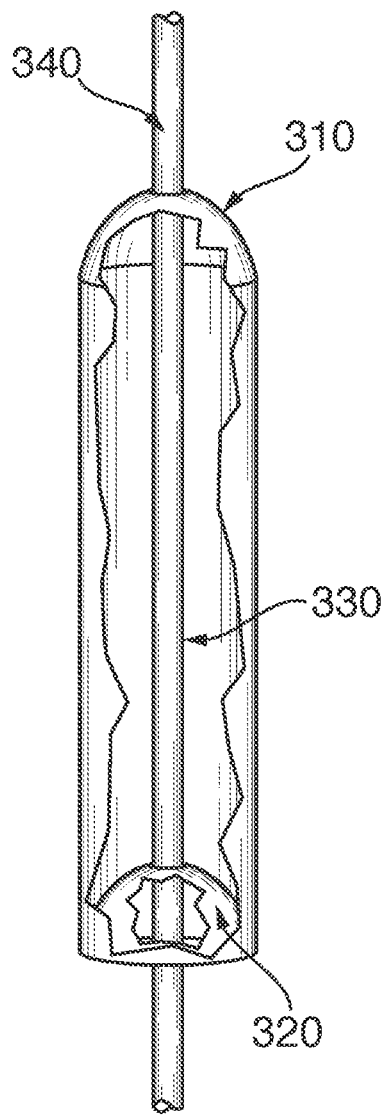
FIGS. 3A and 3B depict detailed views of an example embodiment of a segment for use in an immobilization device.
Figure 3B:
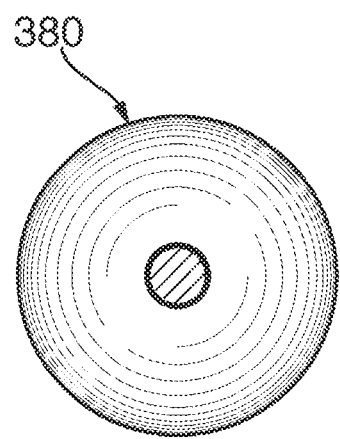

FIGS. 3A and 3B depict two views of a segment 300 for use as a modular component in the pillar of a head and spine immobilization device as depicted in FIGS. 1, 2, 11 and 12. The segment 300 is cylindrical in shape with a convex end 310, a concave end 320 and a hollow lumen 330 centrally located on the cross section of the segment 300 and running along the longitudinal axis of the segment 300. Preferably, the segment 300 is made of a lightweight, durable and stiff material such as carbon fiber, ceramics, metal, metallic alloy or plastic. Furthermore, the segment 300 is preferably heat resistant. The diameter of the segment 300 depends on the level of stabilization required for the immobilization device the segment 300 is integrated into, as a greater diameter will typically be able to withstand greater forces. The length of the segment 300 may also vary between the intended purpose of the immobilization device, and the size of the intended user of the immobilization device, as smaller users may require smaller segments. The example embodiment depicted in FIG. 3A includes a cable 340 running through the lumen 330 of the segment 300. The lumen 330 is a circular hole running the length of the segment 300. However, a person of ordinary skill in the art would recognize the that other shapes may be used. The convex end 310 is spherical and the concave end 320 with a spherical indentation. Again, a person of ordinary skill in the art would recognize that other geometries can be used, such as oval, triangular, square or rectangular. The lumen 330 has a circular opening on both the convex end 310 and concave end 320 of the segment 300. The diameter of the lumen 330 will be sufficient to allow a cable to run through the segment 300 without impedance and minimal friction. However, a person of ordinary skill in the art would recognize that the lumen 330 may have alternative geometries based on its use and the cable intended to run the length of the segment 300. FIG. 3B further shows the spherical outer surface 380 of the segment 300.

While FIGS. 3A and 3B depict the segment 300 having a cylindrical shape, a person of ordinary skill in the art would recognize that different shapes are possible. For example, the cross section of the segment 300 may be oval shaped rather than circular when viewed top down as shown in FIG. 3B, allowing a thinner cross section in one dimension. The cross section of the segment 300 may be triangular, square, rectangular, or any other shape known and convenient.

Figure 4:
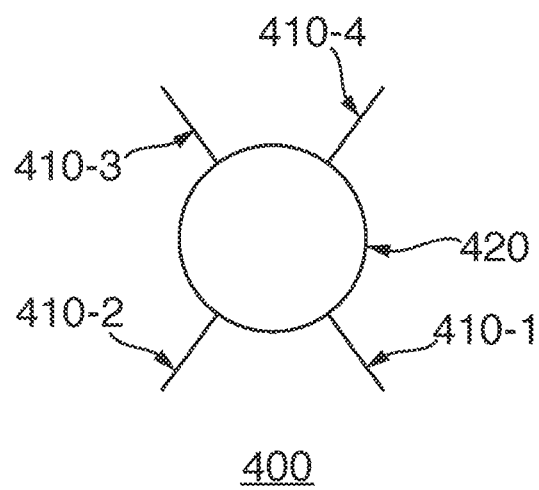
FIG. 4 depicts a detailed view of an example embodiment of a segment with fins for use in an immobilization device.

FIG. 4 depicts additional example embodiment of segment 400 designed with fins 410-1, 410-2, 410-3 and 410-4, respectively, geometrically positioned to confer maximal ergonomic suitability for the segment 400, as well as necessary stiffness or strength, minimizing mass, and weight and for use as a modular component in the pillar of a head and spine immobilization device as depicted in FIGS. 1, 2, 11 and 12. The segment 400 is similar to segment 300 described in reference to FIG. 2. For example, the segment 400 has a similar concave end and concave end, a hollow lumen running along the longitudinal length of the segment 400 and may be made of the same materials. Segment 400 also includes fins 410-1, 410-2, 410-3 and 410-4 that run the length of the segment and convey additional stiffness of a larger diameter segment at a fraction of the weight. The fins 410-1, 410-2, 410-3 and 410-4 will typically be made of the same lightweight and durable material as the segment 400.

Figure 5A:
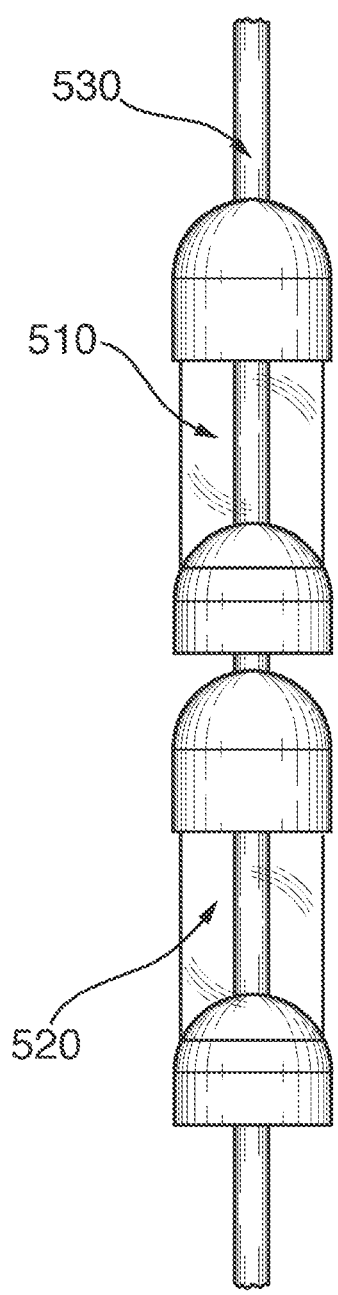
FIGS. 5A and 5B depict detailed views of example embodiment of segments for use in an immobilization device and in activated and inactivated states.
Figure 5B:
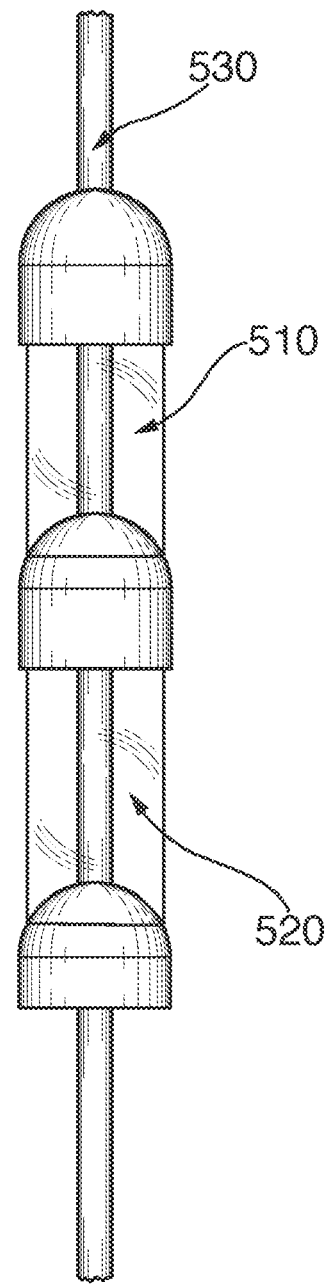

FIGS. 5A and 5B depict a detailed view of segments 510 and 520 in inactivated and activated states. The segments 510 and 520 are similar to the segments described in FIGS. 3A, 3B, 4, 10A, 10B, 100, 13A, 13B, 14A, 14B, 15A, 15B, 16A, 16B, and 17, and are typically used in the pillars described in reference to FIGS. 1, 2 and 11, which consist of the segments and the cable 530 that runs through the lumen of the segments 510 and 520. When the segments 510 and 520 are in the non-activated configurations depicted in FIG. 5A, the pillar is flexible and able to bend. FIG. 5B depicts the segments in the activated configuration; the pillars confer rigidity, and thus resistance motion of the head and spine. In FIG. 5B, the segments 510 and 520 are keyed together by restricting the cable 530 running through the lumen of the segments 510 and 520, subsequently the segments are pushed and/or translated together. There are several options for activation of immobilization device. For example, several cable or wire locking mechanisms may be used, as described in FIGS. 6, 7, 8A, 8B and 12.

Figure 11:
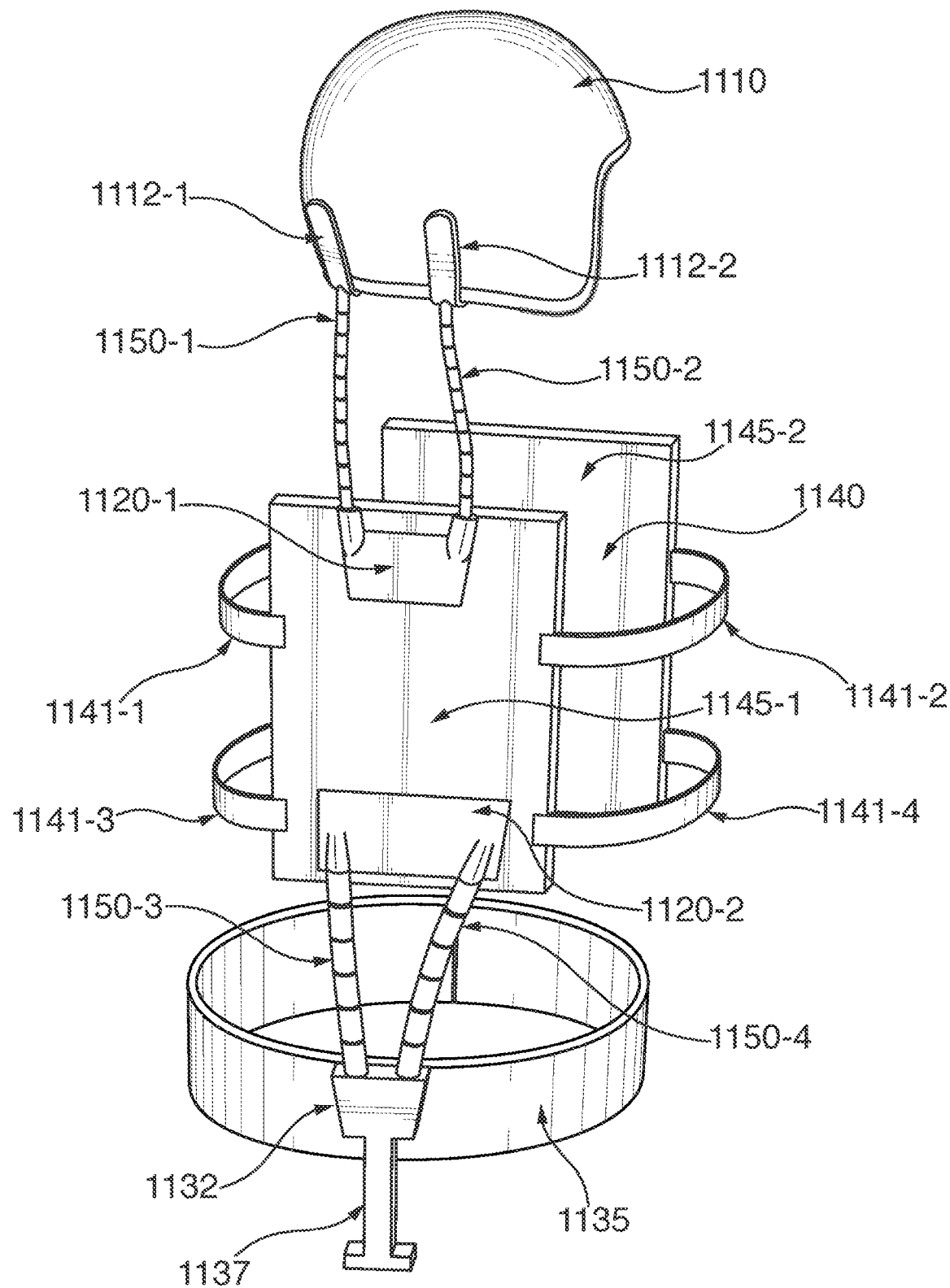
FIG. 11 depicts an example embodiment of an immobilization device with a vest, a belt and caudal extension, and with segments exposed.

Furthermore, FIGS. 5A and 5B are illustrative only and multiple segments may be used, all of which will be keyed together, concave end of one segment keyed into the convex end of the next segment when the pillars are activated. Typically, at the attachment points of the immobilization device, such as shown in FIGS. 1, 2 and 11, special terminating segments are used and affixed to the attachment points. In particular, the most proximal segment to the attachment point is fixed to the attachment point and—if there is one at this attachment point—the cable or wire tightening mechanism. The terminating segments can be glued, welded, screwed, or bolted to the attachment point, or affixed using any other method known and convenient.

Figure 6:
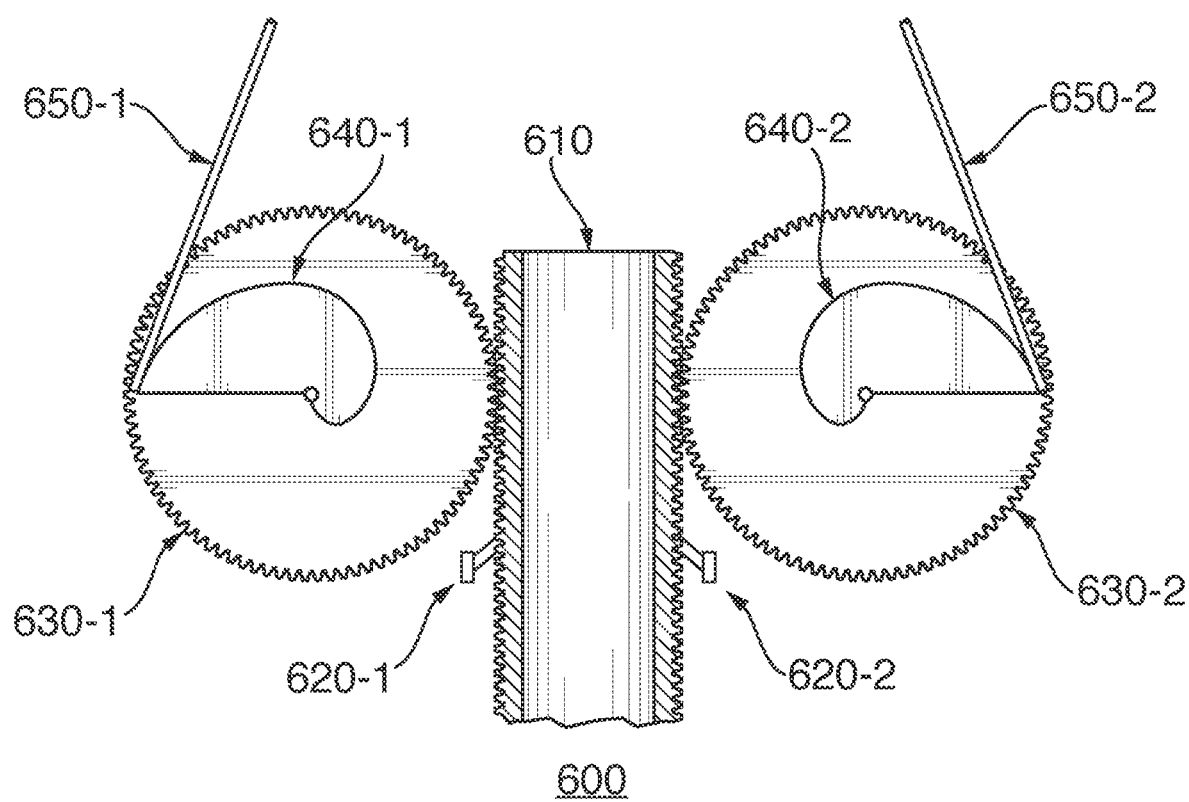
FIG. 6 depicts a detailed view of an example embodiment of a gear locking mechanism for pillars in an immobilization device.

FIG. 6 depicts a detailed view of an example embodiment of a gear locking mechanism 600 for pillars in an immobilization device. One of the possible tightening mechanisms (regardless of the energy source e.g. compressed gas, pyrotechnics) for use in an immobilization device will tighten the cable or wire by a piston 610 an engaging a locking mechanisms 620-1 and 620-2 that will prevent the backwards motion and will lock the piston 610 in place. The piston 610 rotates two gears 630-1 and 630-2 using a rack and pinion mechanism. The gears 630-1 and 630-2 include teeth that interlock with teeth on the piston 610 and when the piston 610 is moved gears 630-1 and 630-2 rotate. Each of the gears 630-1 and 630-2 are attached to coaxial gears 640-1 and 640-2, respectively, with the coaxial gears 640-1 and 640-2 having a progressively smaller diameter.

Gear locking mechanism 600 can be used to activate the pillars shown in FIGS. 1, 2 and 11 and can be located in the vest, helmet, belt or any other location known and convenient. To activate, a force will be asserted in the piston 610, causing the piston 610 to shift upward, rotating the gears 630-1 and 630-2, and by transference, the coaxial gears 640-1 and 640-2. The coaxial gears 640-1 and 640-2 work as reels to coil the cables 650-1 and 650-2, respectively, causing the cables 650-1 and 650-2 to tighten. The differential diameter of coaxial gears 640-1 and 640-2 offers a rapid initial tightening of the slack cable and at the end of tightening the smaller diameter will lead to a tightening with greater torque, achieving a high degree of tension on the cables 650-1 and 650-2. This mechanism will tighten the cable and to cause the activation of the pillars described in FIGS. 1 and 2, through the locking of the segments described in FIGS. 5A and 5B.

Figure 7:
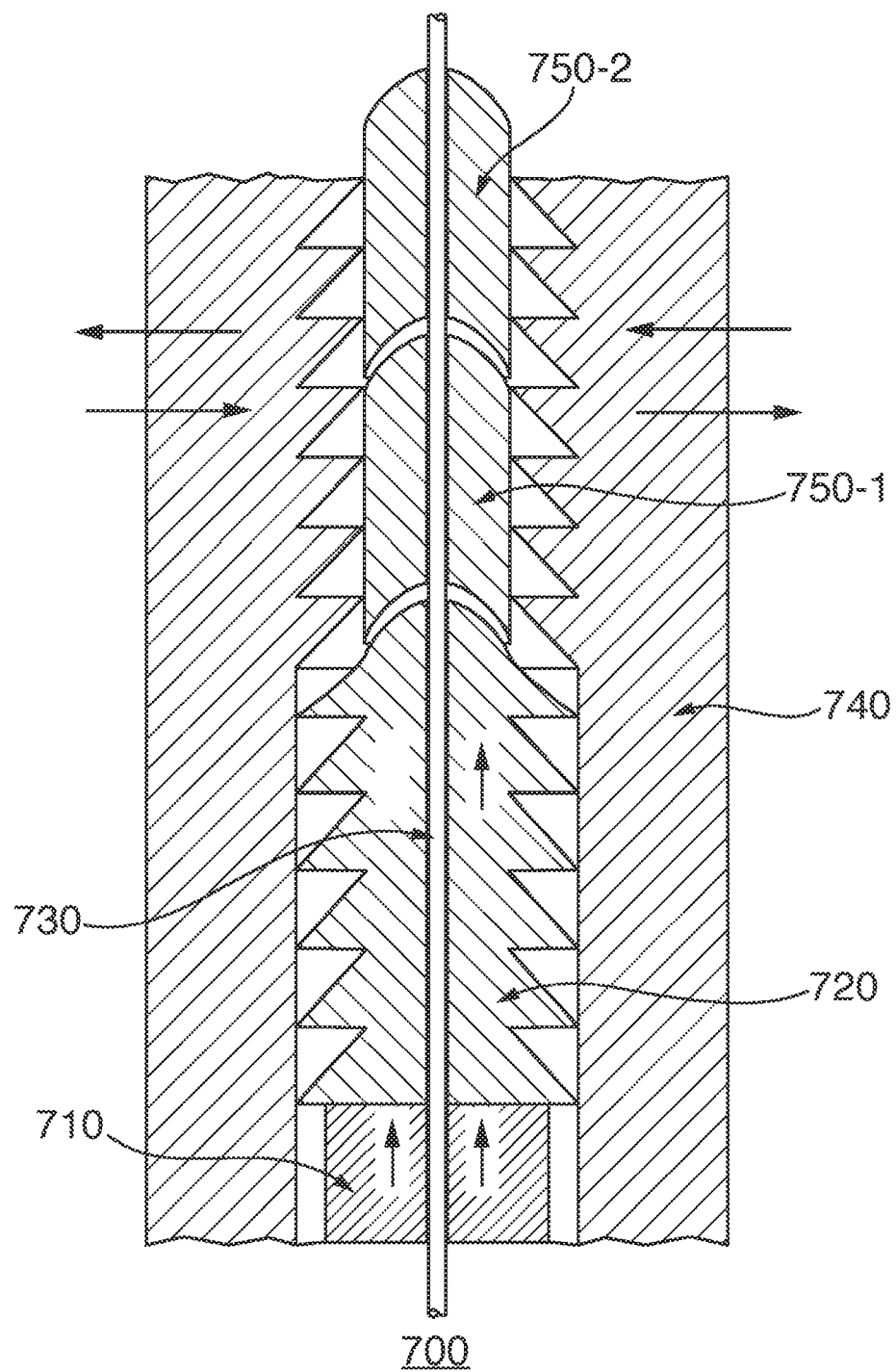
FIG. 7 depicts a detailed view of an example embodiment of a locking mechanism for pillars in an immobilization device.

FIG. 7 depicts a detailed view of an example embodiment of a piston and ratchet locking mechanism 700 for pillars in an immobilization device. Locking mechanism 700 includes a chamber 710, locking piston 720, cable 730, interlocking peripheral component 740 and segments 750-1 and 750-2. Locking mechanism 700 may be activated by compressed gas, spring or pyrotechnic charge within a chamber 710 that when activated drives the locking piston 720 into the concave section of the segment 750-1 which in turn keys into segment 750-2. In some example embodiments, a piston pushes into the convex portion of a segment (depending on the direction of the pillar).

The locking piston 720 engages a ratcheted mechanism in a forceful fashion that pushes up into segment 750-1 and locks the individual segments. This figure only shows segments 750-1 and 750-2, but typically a number of segments would be after segment 750-2, but not depicted in this figure. These segments would continue the length of a pillar, as discussed in reference to FIGS. 1, 2, 5A, 5B, 11 and 12. The interlocking peripheral component 740 of locking mechanism 700 affords elastic expansion during the ascent of the locking piston 720 in the chamber 710, and then immediate retraction to effectively lock the locking piston 720 in place with the teeth of the interlocking peripheral component 740. The interlocking peripheral component 740 may be segmented and include an elastic material and/or device (e.g. spring) to effect this type of expansion and retraction. Alternatively, the interlocking peripheral component 740 is not be segmented and instead made of a material with elastic properties to achieve this desired mechanism. Alternatively, the interlocking peripheral component 740 includes a hinged safety allowing movement only to one direction (towards tightening the pillar) and will not permit any movement to the opposite direction. The cable 730 is anchored to the interlocking peripheral component 740. The ratchet locking mechanism 700 can be used to activate the pillars shown in FIGS. 1, 2, 11 and 12, and can be located in the vest, helmet, belt or any other location known and convenient.

An additional example embodiment, to the piston/ratchet mechanism will use the same ratchet and piston mechanism and a cable terminates into the piston. In this example embodiment, instead of pushing the segments together, upon activation of a charge, spring or compressed gas, pistons at opposite ends of the pillar move in opposite directions resulting in pillar activation, and thereby rigidity of the pillar. In some example embodiments, for example if the system is attached to the cervical spine/head, then only one piston moves upward to active the pillar. Thus, the type of locking mechanism incorporated in the user's vest will be predicated on the portion of the body targeted for protection. The ratio of allowable motion of either pillar is designed to maximize rigidity while minimizing motion and recoil of the head or back.

An additional example embodiment, the locking of the segments of the pillars is initiated in a gas chamber, located in the vest of the user, into which compressed gas is injected during system activation. This will cause a rapid rise in pressure that will push a drive piston in the desired direction. The drive piston will be solid with a central hole to accommodate the cable or wire used in the system. The drive pistons will have a several O-rings to maintain pressure within the gas chamber. A rise in pressure inside the gas chamber will push the drive pistons in the desired direction. The drive piston and the internal walls of the gas chamber will have mechanical excursion blocks to limit the movement of the drive pistons. The movement of the drive pistons, in turn, pushes the segments of the pillars in the desired direction to the desired excursion which, in turn, causes activation, or locking, of the system. Deactivation of the system can be manual or automatic. Both the latter and former will involve opening a temporarily opening a gas efflux valve to cause an efflux of the compressed gas to the environment thereby deactivating the system and conferring flexibility to the system again. The drive pistons within the gas chamber(s) may be spring loaded (not pictured) to ensure recoiling into the proper "start" position.

In some example embodiments, the fast activation or tightening mechanism for the pillars may be a pyrotechnic or a compressed gas mechanism activated by an activation mechanism. In applications where rapid activation (causing pillars to become rigid) and tightening is not necessary, then a manual-tightening device can be used, such as an electric motor. In applications where repetitive activation is needed (e.g. fighter pilot version) an electrical or hydraulic tightening system can be used.

Figure 8A:
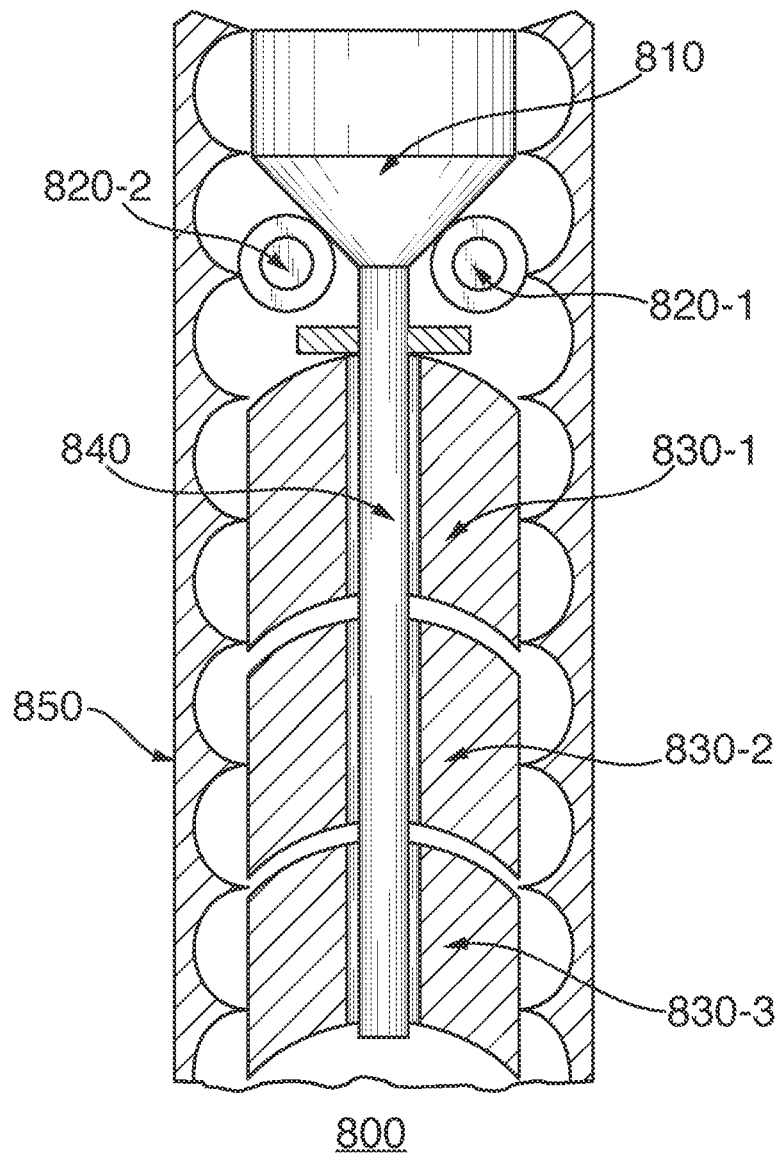
FIGS. 8A and 8B depict detailed views of example embodiments of a locking mechanism for pillars in an immobilization device utilizing a piston and ratchet locking mechanism.
Figure 8B:
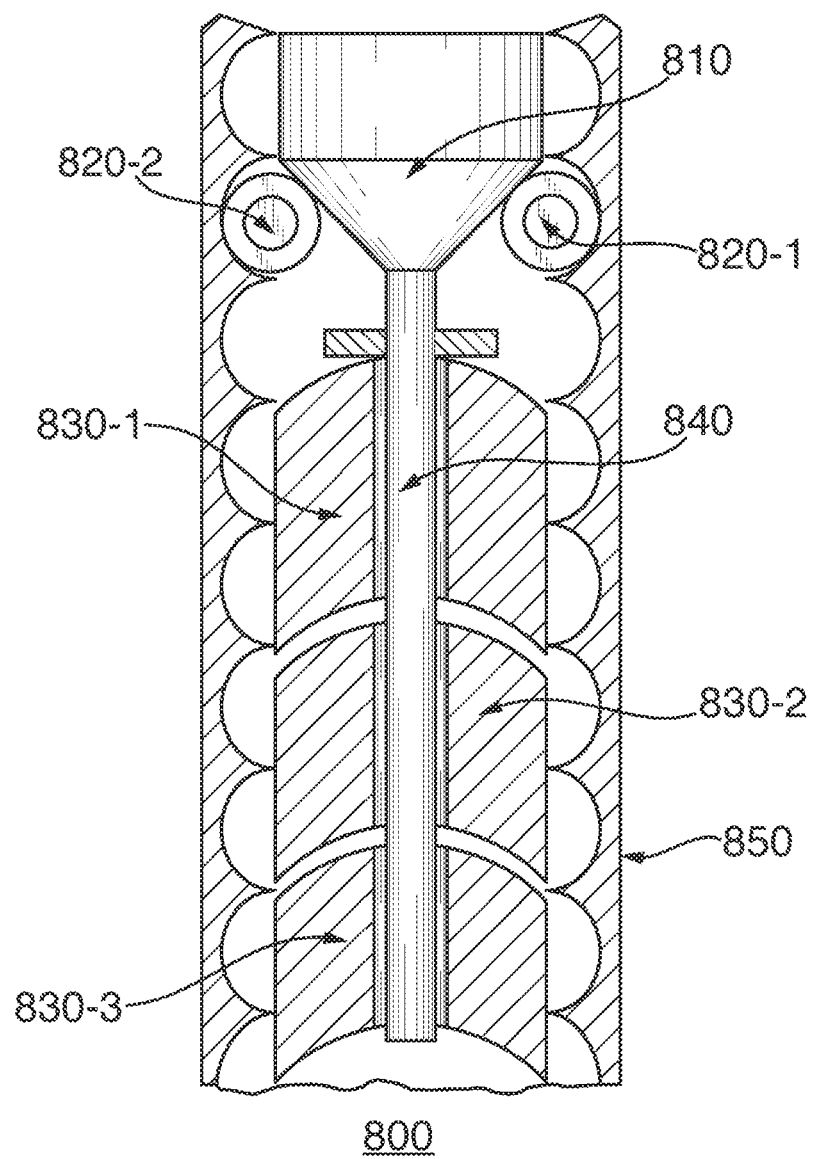

FIGS. 8A and 8B depict detailed views of example embodiments of a telescoping locking mechanism 800 for a pillar in an immobilization device utilizing a piston and ratchet locking mechanism. The locking mechanism 800 includes a wedge end piece 810, rollers 820-1 and 820-2, segments 830-1, 830-2, and 830-3, cable 840, and interlocking peripheral component 850. The telescoping locking mechanism 800 is used in a pillar connected to the cable 840 that runs inside the segments 830-1, 830-2, and 830-3. The interlocking peripheral component 850 includes ridges that are peripherally located in its inner surface creating multiple recesses. The width of the wedge end piece 810 is smaller than the distance between the tips of the ridges in the interlocking peripheral component 850 (inner diameter) to allow for the free movement of the wedge shaped end piece 810. When the locking mechanism 800 is not activated the roller 820-1 and 820-2 lie within the tips of the lateral recesses of the interlocking peripheral component 850 and allow the free movement of the wedge shaped end piece 810 in a pillar. When the system is activated, a sudden tightening force is applied to the cable 840 that is transmitted up to the cranial end of the pillar in which the locking mechanism 800 is used. The sudden acceleration of the wedge shaped end piece 810 forces the cylindrical rollers 820-1 and 820-2 in the direction the cable 840 is tightened and forms a 45-degree angle to the tightening axis of the cable 840. This force causes the outward movement of the cylindrical rollers 820-1 and 820-2 to engage with the recesses inside the interlocking peripheral component 850. The engagement of the cylindrical rollers 820-1 and 820-2 to the locking recesses of the interlocking peripheral component 850 stabilizes this way the cranial end of the pillar in relation to the receptor, when traction forces develop between the peripheral component 850 and the internal components. If the forces that develop between the peripheral component 850 and the internal components are compression forces, the stability is achieved by a short delay in the return of the rollers 820-1 and 820-2 in their inner position (the inner position normally allows free movement). This delay would allow the most cranial segment 830-1 to engage against the rollers and stop any further compression movement. The telescoping locking mechanism 800 can be used to activate the pillars shown in FIGS. 1, 2, 11 and 12, and can be located in the vest, helmet, belt or any other location known and convenient.

Figure 9:
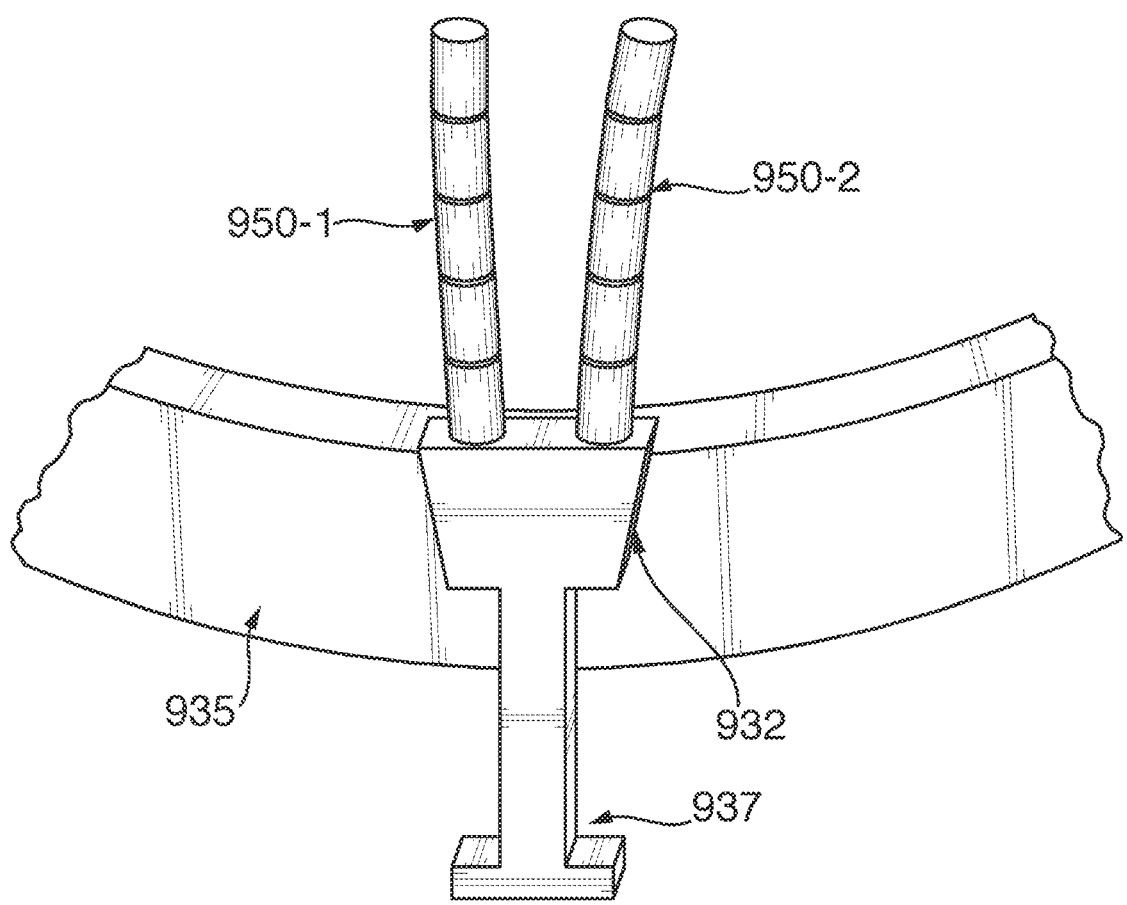
FIG. 9 depicts a caudal extension.

FIG. 9 depicts a detailed view of an immobilization device with a caudal extension 937. Typically, the caudal extension 937 will be a few centimeters long, extending down approximately to the tip of the coccyx, rigid and connected to the caudal end of the pillars 950-1 and 950-2 and the belt 935 by attachment point 932. The caudal extension 937 prevents the adverse effects or vertical acceleration (e.g. explosion underneath a vehicle). The caudal extension 937 will transfer the weight of equipment (e.g. helmet, vest) and part of the body weight directly to the seat, offloading, or splinting the immense forces from the spine and lead to injuries. The caudal extension 937 can be connected to a receptor in the seat in the vehicle the user is traveling in and in this case the immobilization system would offer an immobilization of the person to the seat, negating the need for safety belts. In such a case, the person would have greater mobility compared with using the safety belt, while enjoying a greater degree of protection when the immobilization system is activated. The caudal extension 937 is shown with a "T" configuration, but a person of ordinary skill in the art would understand that a number of geometries are possible based on the anticipated application. For example, if the caudal extension is intended to be inserted in a receptor in a seat, the caudal extension can have a tongue shape commonly used with seat belts to be inserted into a buckle.

Figure 10A:
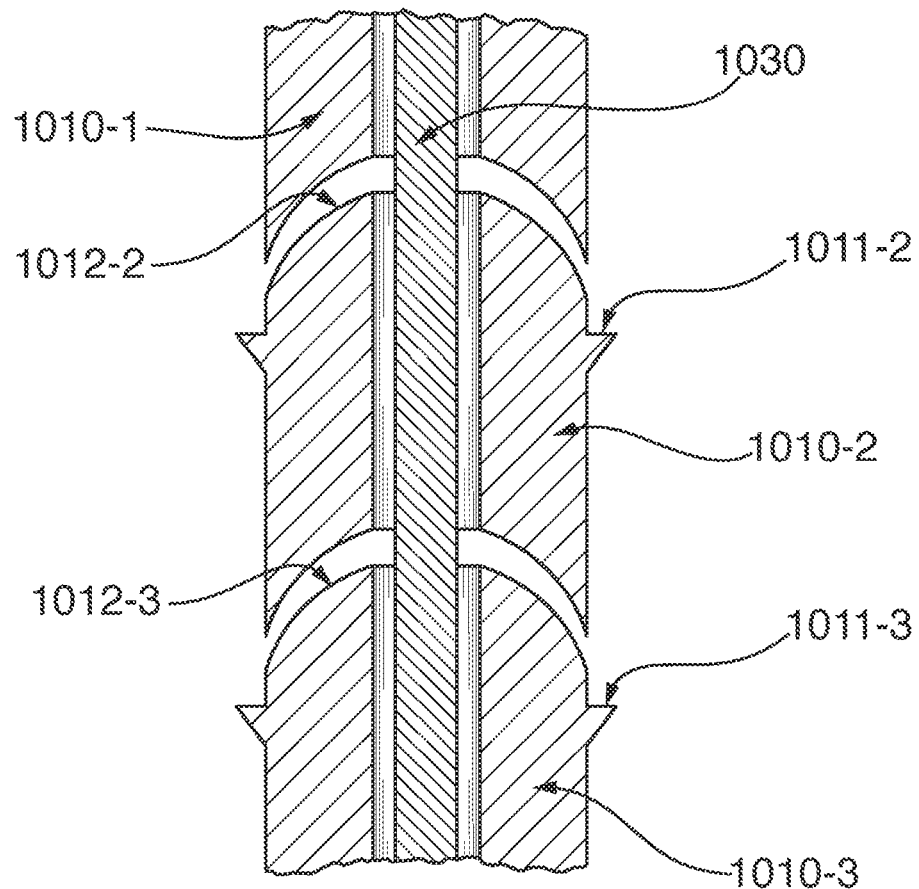
FIGS. 10A, 10B and 10C depict a detailed view of the cross section of example embodiments of segments for use in an immobilization device.

FIG. 10A depicts a detailed view of the cross section of example embodiments of segments for use in an immobilization device. The cable 1030 runs through the lumen of segments 1010-1, 1010-2 and 1010-3. Segments 1010-1, 1010-2 and 1010-3 include peripheral projections 1011-2 and 1011-3, and curved surfaces 1012-2, 1012-3 (segment 1010-1 would include a peripheral projection and a curved surface as well, but is not shown in FIG. 10A). FIG. 10A is a cross section view of the segments 1010-1, 1010-2 and 1010-3 and the Peripheral projections 1011-2 and 1011-3 would typically wrap around the entire exterior of the typically circular exterior of the segments 1010-1, 1010-2 and 1010-3. Peripheral projections 1011-2 and 1011-3 are an optional configuration of the segments 1010-1, 1010-2 and 1010-3 and prevent bending of two adjacent segments beyond a certain angle, which can be determined by the size and geometry of the peripheral projection. The exact location of the peripheral extensions 1011-2 and 1011-3 in regards to their distance from the curved surface 1012-2 and 1012-3 can be designed to limit the bending within the normal range of motion at the various spinal regions. This special design would place the peripheral projection at different distances from the convex surface at the anterior, lateral, posterior aspects of the segment, simulating the different flexion/lateral flexion/extension range of motion of the various spine regions. The peripheral projections 1011-2 and 1011-3 are shown with a straight edge and point, but other shapes, such as a rounded or semicircular projection can be used in the alternative. The peripheral extensions can serve as a fail-safe mechanism, in case the friction forces between the concave-convex ends of the segments fail to stabilize the system against severe forces.

Figure 10B:
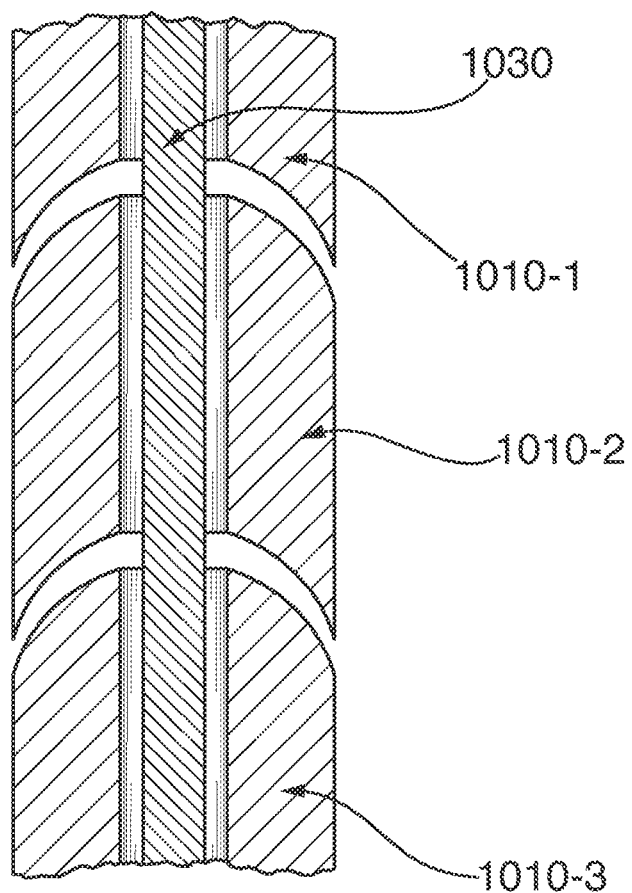

FIG. 10B depicts a detailed view of the cross section of example embodiments of segments for use in an immobilization device. The segments 1010-1, 1010-2 and 1010-3 in FIG. 10B are similar to FIG. 10A, however are shown without peripheral extensions. Segments 1010-1, 1010-2 and 1010-3 include convex and concave curved surfaces. The curved surfaces can be coat in enamel or other material to achieve optimum friction between the segments when used in an immobilization device.

FIG. 10O depicts a detailed view of the cross section of an example embodiment of segments for use in an immobilization device with dentate peripheral projections. The segments 1010-1, 1010-2 and 1010-3 in FIG. 10O are similar to FIGS. 10A and 10B. However, segments 1010-1, 1010-2 and 1010-3 include a covering with dentate peripheral projections 1011-2, 1011-3, 1012-1 and 1012-2. Dentate peripheral projections 1011-2, 1011-3, 1012-1 and 1012-2 are an optional configuration of the segments 1010-1, 1010-2 and 1010-3 and limit rotation motions. The dentate peripheral projections 1011-2, 1011-3, 1012-1 and 1012-2 limit both bending and rotational forces, including those exceeding the friction force of segments when the system is activated. The dentate peripheral projections include teeth that interlock when the segments are compressed through activation, as described in FIGS. 1, 2, 5A, 5B and 11.

FIG. 11 depicts an example embodiment of an immobilization device 1100 with a vest 1140, a belt 1135 and caudal extension 1137, and showing pillars 1150-1, 1150-2, 1150-3 and 1150-4 with exposed segments. The immobilization device 1100 shares many components with the immobilization devices depicted in FIGS. 1 and 2. The immobilization device 1100 includes a helmet 1110, a vest 1140 and pillars 1150-1, 1150-2, 1150-3 and 1150-4. The helmet 1110 includes helmet attachment points 1112-1 and 1112-2. The vest 1140 includes a back vest portion 1145-1 and a front vest portion 1145-2, attachment points 1120-1 and 1120-2, chest straps 1141-1, 1141-2, 1141-3 and 1141-4. The helmet 1110 attaches to the vest 1140 with pillars 1150-1 and 1150-2. The vest 1140 attaches to the belt at belt attachment point 1132.

The immobilization device 1100 includes pillars 1150-1, 1150-2, 1150-3 and 1150-4 where the individual segments are visible in the pillars. However, in other embodiments the segments will be covered with a sheath or outer covering to avoid wear on the segments and to avoid blocking or hindering the operation of the segments, for example through clothing being caught in-between segments when the immobilization device is activated. The segments used in pillars 1150-1, 1150-2, 1150-3 and 1150-4 can be any of those described in reference to FIGS. 3A and 3B, 4, 5A, 5B, 10A, 10B, 10O, 13A, 13B, 14A, 14B, and 17. The segments in pillars 1150-1, 1150-2, 1150-3 and 1150-4 may be locked in place with a locking mechanism that can be in attachment point 1120-1, 1120-2 and/or belt attachment point 1132. The locking mechanism can be any of those described in reference to FIGS. 6, 7, 8A and 8B. Further detail on the caudal extension 1137 can be seen in reference to FIG. 9. The immobilization device 1100 can be activated as described in reference to FIGS. 1, 2, 5A and 5B.

The back vest portion 1145-1 and a front vest portion 1145-2 will typically be constructed of a durable and non-flexible material. For example, lightweight metals, composite materials, ceramics can be used depending on the application. In certain applications, the back vest portion 1145-1 and front vest portion 1145-2 will also serve as protections from ballistics, such as protection from bullets or protection from debris from a blast. The back vest portion 1145-1 and front vest portion 1145-2 may be contoured in some applications to fit more comfortably against the user. Furthermore, in some example applications, the back vest portion 1145-1 and front vest portion 1145-2 will be embedded within a flexible and comfortable material, such as cloth and worn as clothing.

Figure 12:
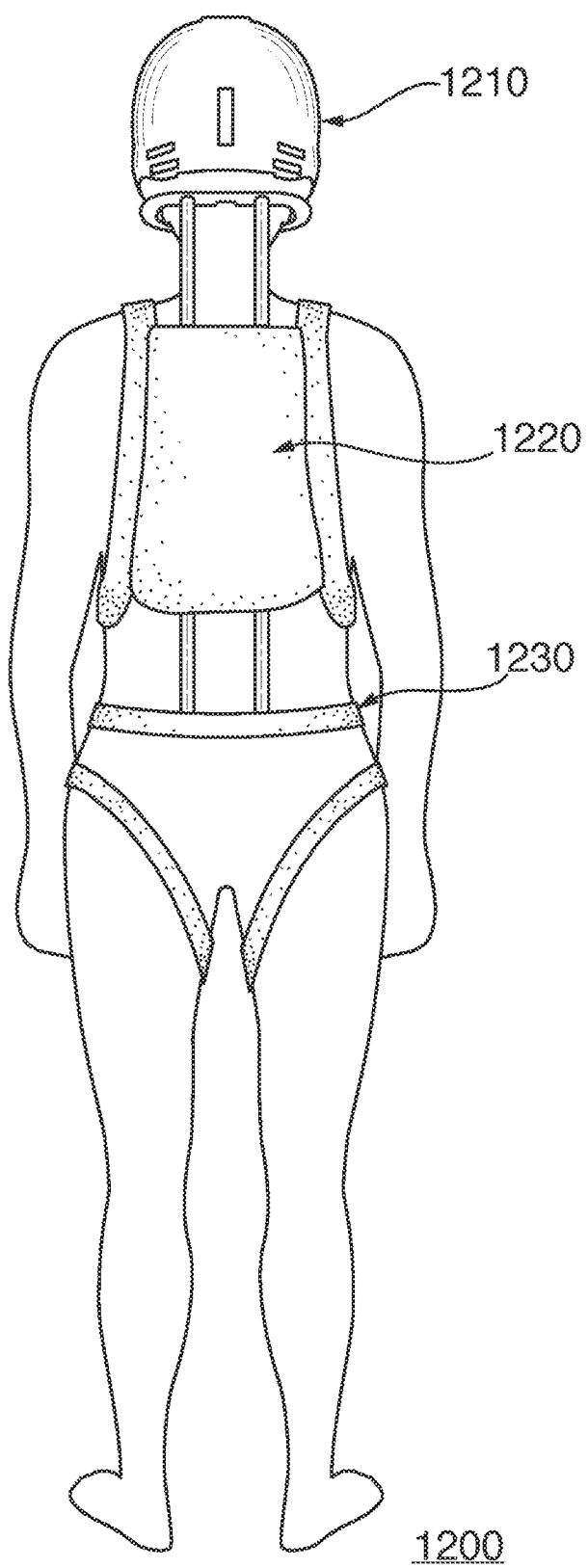
FIG. 12 depicts an alternative embodiment of an immobilization device with a helmet, a vest and a belt.

FIG. 12 depicts an alternative embodiment of an immobilization device 1200 with a helmet 1210, a vest 1220 and a belt 1230. The immobilization device 1200 is designed to act as an exoskeleton or external brace by channeling the axial forces to the device and away from the person's body. This external splint will prevent brain and spinal injury.

One end of the pillars used in the immobilization device 1200 is securely connected to the posterior aspect of the helmet 1210, while the other end is connected to the housing apparatus in the vest 1220. The housing apparatus in posterior aspect of the vest 1220 is designed to be the lower terminal connection of the pillars for head and upper spine protection, or the upper terminal connection for lower spine and sacrum protection. The housing apparatus allows translation and/or telescoping and/or rotation of the pillars to accommodate necessary motion pillar motion during the normal ranges of bodily motion. For example, during normal neck forward flexion, the housing apparatus will allow the pillar system to lengthen in a controlled manner.

Figure 13A:
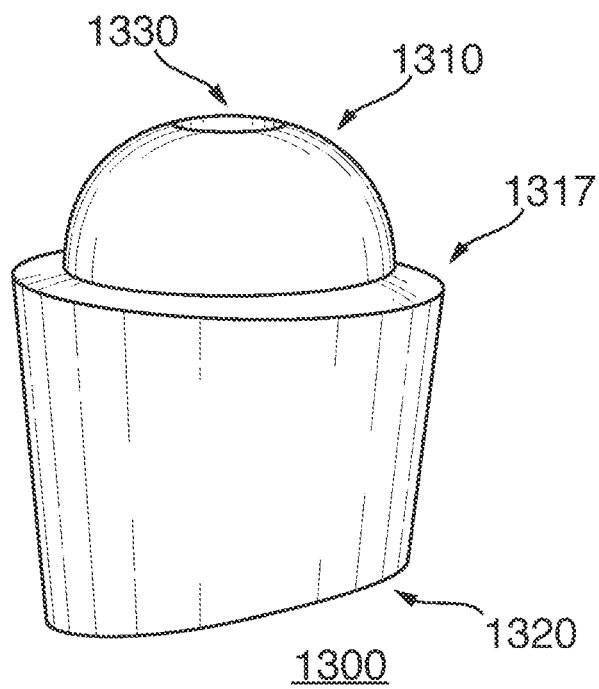
FIGS. 13A and 13B depict detailed views of an example embodiment of a segment for use in a pillar in an immobilization device.
Figure 13B:
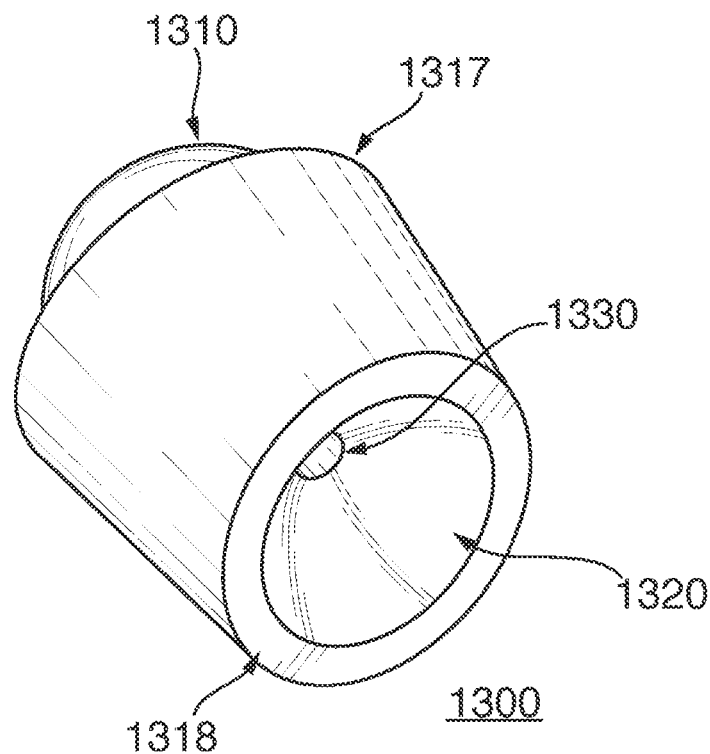

FIGS. 13A and 13B depict detailed views of an example embodiment of a segment 1300 for use in a pillar in an immobilization device. FIGS. 13A and 13B depict two views of the segment 1300 for use as a modular component in the pillar of a head and spine immobilization device, such as depicted in FIGS. 1, 2, 11, and 15. Similar to the segment shown in FIGS. 3A and 3B, the segment 1300 is generally cylindrical in shape with a convex end 1310, a concave end 1320 and a hollow lumen 1330 centrally located on the cross section of the segment 1300 and running along the longitudinal axis of the segment 1300. However, the segment 1300 tapers so that the diameter of the segment 1300 is greater at the convex end 1310 than at the concave end 1320 of the segment 1300. The degree of tapering in the segment 1300 can be varied based on the use of the segment, but, preferably, the segment will taper between 1 to 30 degrees relative to the longitudinal axis of the segment 1300. The segment 1300 also includes a first lip 1317 surrounding the convex end 1310, which first lip 1317 is at an angle to the lateral axis of the segment 1300. The first lip 1317 can be used at a number of angles that are known an convenient for the application, in some embodiments it will be between 1 to 15 degrees relative to the lateral axis of the segment 1300, although other angles are possible and can be greater angle depending on the operational requirements of the segment 1300 and the immobilization device the segment 1300 will be used. The segment 1300 also includes a second lip 1318 surrounding the concave end 1320. The second lip 1318 is at an angle to the lateral axis of the segment 1300, and as depicted, the second lip 1318 can have a greater angle than the first lip 1317, such as 3 to 25 degrees relative to the lateral axis of the segment 1300. However, other angles are possible for the second lip and can be greater or less depending on the operational requirements of the segment.

The segment 1300 shown in FIGS. 13A and 13B is similar to the segment shown in FIGS. 3A and 3B, in that it can have a number of different geometries and material compositions, depending on the particular application. The segment 1300 can also similarly be used as part of a pillar, which provides stability based on the interlocking of segments when a cable running through the hollow lumen 1330 is tightened, causing the segments to interlock convex end to concave end. Furthermore, the relative amount of tapering, the angles of the first lip 1317 and second lip 1318 can be varied for different segments within a pillar. For example, segments in certain sections of the pillar must allow for more motion (e.g. flexion, extension, lateral bending, coupled motions), than segments in other section of the pillar. Furthermore, the amount of spine motion may vary relative to the part of the body of the user of the immobilization device the segment 1300 is used in, so that segments of different geometry can be used within the same pillar, based on the required amount of motion required. Specifically, the length and diameter of the segments, as well as the geometries of the convex and concave articulations in the segments of the pillar can all be modified to achieve the desired motion for a specific section of the pillar subsystem.

Figure 14A:
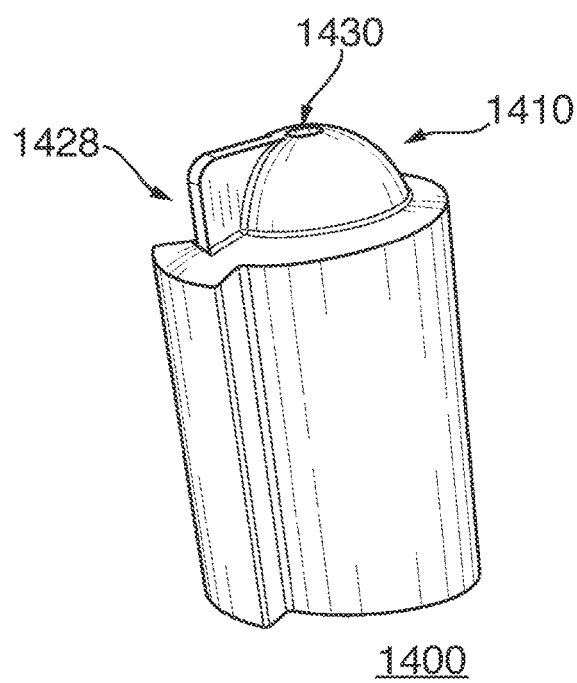
FIGS. 14A and 14B depict detailed views of an example embodiment of a segment with a flat protrusion and for use in a pillar in an immobilization device.
Figure 14B:
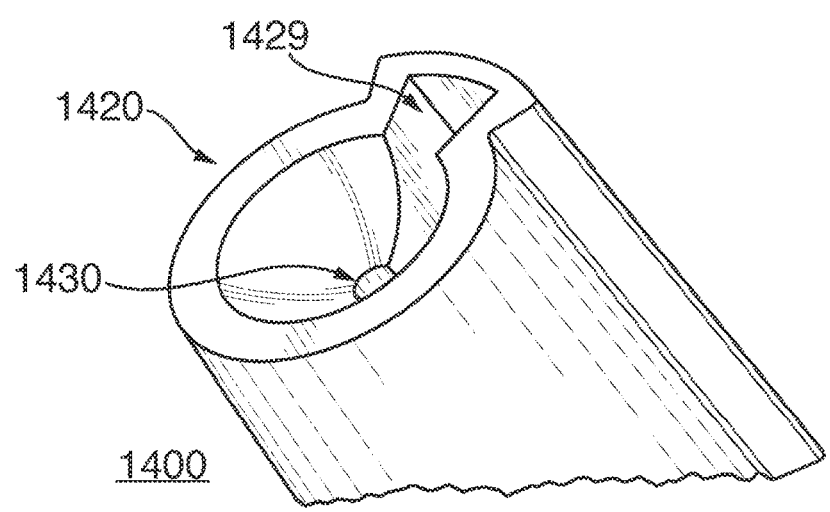

FIGS. 14A and 14B depict detailed views of an example embodiment of a segment 1400 with a flat guide protrusion 1428 and flat guide indentation 1429 and for use in a pillar in an immobilization device. FIGS. 14A and 14B depict two views of a segment 1400 for use as a modular component in the pillar of a head and spine immobilization device, such as depicted in FIGS. 1, 2, 11, and 15. The segment 1400 can include geometries and compositions similar to those shown in a segment in FIGS. 3A, 3B, 13A, 13B, 15A, 15B, and 17, or a combination of both, depending on the required application. The primary difference in segment 1400 from the segments shown in those figures, is the inclusion of a flat guide protrusion 1428 and flat guide indentation 1429. The segment 1400 shown in FIGS. 14A and 14B is generally cylindrical in shape with a convex end 1410, a concave end 1420 and a hollow lumen 1430 centrally located on the cross section of the segment 1400 and running along the longitudinal axis of the segment 1400. As discussed above in relation to the segment in FIGS. 3A and 3B, the segment 1400 can be a number of materials and size ratios, depending on the parameters of the intended use. The convex end 1410 of the segment 1400 is generally spherical and includes a flat guide protrusion 1428. The concave end 1420 of the segment 1400 has a spherical indentation and flat guide indentation 1429. The convex end 1410 and concave end 1420 have similar properties to those described in reference to the segment in FIGS. 3A and 3B. The flat guide protrusion 1428 and flat guide indentation 1429 in segment 1400 are reciprocal in geometry, in that the flat guide protrusion 1428 fits inside of the flat guide indention 1429, and both are oriented parallel to the longitudinal axis of the segment 1400. The lumen 1430 has a circular opening on both the convex end 1410 and concave end 1420 of the segment 1400. The diameter of the lumen 1430 will be sufficient to allow a cable to run through the segment 1400 without impedance and minimal friction. The flat guide protrusion 1428 and flat guide indentation 1429 can be utilized to provide a pillar with increased stability across several axes, as the flat guide protrusion 1428 and flat guide indentation 1429, when used in an immobilization device, increase the resistance to rotational forces because the flat guide protrusion 1428 and flat guide indentation 1429 provide a mechanical block to rotational movement at the segment to segment level, as shown in greater detail in reference to FIGS. 14A and 14B. As such, the flat guide protrusion 1428 provide a mechanical stop in the flat guide indentation 1429, and thus to add further stability to the system during large loading forces that can cause harmful head and neck flexion, extension, rotation, lateral bending, and coupled motions (i.e combinations of directions like rotation and lateral bending. The flat guide protrusion 1428 and flat guide indentation 1429 are interlocking when the immobilization device is inactivated and activated, thereby providing this resistance to rotational forces both even before the immobilization device has been activated.

In certain example embodiments only certain segments within a pillar will have a flat guide protrusion and/or flat indentation, as described in FIGS. 14A and 14B, depending on the location of the segment relative to the anatomy of the user. For example, in certain areas such as corresponding to the user's waist, greater flexibility is desirable. In other areas, such as in the user's mid-back, rotational flexibility is of a lesser importance. By using the segments with flat guide and indentation portions in the mid and upper back of the user, the immobilization device provides increased protection, while minimizing the constraints on the user's motion. The indentation can be wider that the protrusion to allow for some limited rotational motion.

In the example embodiment of segment 1400 depicted in FIGS. 14A and 14B, the segment 1400 limits the inter-segmental motion and prevents each segment from dislocating relative to their adjacent segment using the flat guide protrusion 1428 and a flat guide indentation 1429. This configuration confers great resistance to extension loading on the segment 1400 by buttressing (i.e. thicker in the anterior-posterior plane) the posterior aspect of the pillar system, preventing intersegment dislocation due to segment spinning, allowing a specified and predetermined amount of rotation in-between each segment in way that will correlate, and mimic, the rotation of the spine that that portion of the device is protecting, and providing additional system rigidity to rotational forces that may have otherwise gone beyond safety thresholds. On the superior, convex portion of each segment the flat guide protrusion 1428 will protrude on the posterior portion of each segment. Similarly, the flat guide indentation 1429 on the inferior, concave aspect of each segment 1400. The flat guide indentation 1429 can be wider than its corresponding flat guide protrusion 1428 with which it mates; thus, allowing rotational movement of an amount specified by its geometry and is a scalable feature that can be modified based on the amount of rotation desired. The flat guide indentation can be configured to allow 1-25 degrees of rotation, depending at the location the segment 1400 is used relative to the anatomy of the user.

As another example of the system's necessary scalability, the segment 1400 near (C1-2) can be made to have more rotation to mimic normal human motion. Therefore, the flat guide protrusion 1428 be wider than segments in the lower portions of the neck that have smaller degrees of normal rotation. Other changes in geometry can provide a mechanical block to intersegmental motion, including as an example, a ball/socket design.

Segment 1400 described in FIGS. 14A and 14B can be used to provide tailored limits on flexibility of the pillars of the systems, for example, when used as segments in FIGS. 1, 2, 9, 11, 12, 23A, and 23B. In these cases, the upper portion of the cervical spine between vertebral segments 1 and 2 (C1-2) accounts for 50% of left and right rotation as a person turns their head. The remaining 50% of the neck rotation is divided relatively equally in the remaining lower cervical vertebral segments (C2-T1). The segments 1400 can be used in the systems to mimic these important details of human anatomy by modifying the size of the respective flat guide indentation, with a wider indentation allow greater rotation, and a smaller indentation allowing less rotation.

The size and geometry of segments 1400 depicted in FIGS. 14A and 14B are scalable. For example, for applications requiring more resistance to larger forces (e.g. a fighter pilot with a heavier helmet that is susceptible to larger forces to the head and neck upon ejection from the plane) the size of the segments are increased to meet the loading demands.

FIGS. 14A and 14B can have an arc radius and the circumference of the convex and the corresponding concave mating surfaces will also be scalable to the mimic the motion of the spinal segment it is protecting. Typically, 50% of the cervical spine flexion and extension occurs at the cranial-cervical junction (O-C1), and the remaining such motion is divided relatively equally in the lower cervical segments (C2-T1). Thus, the segments near the upper cervical spine must be able to accommodate such motion. These segments, therefore, will be wider, and the arc radius and the circumference of the convex and the corresponding concave mating surfaces will similarly need to be larger than segments closest to the lower cervical spine. In some example embodiments, the superior aspect of each segment will have a slightly curved downward lateral lip on both sides to allow inter-segmental lateral bending. There will be a corresponding mating surface on the inferior aspect of each segment. The lateral bending of the cervical spine is coupled with rotation, meaning as one laterally bends their neck, there is also rotational motion occurring at the same segment(s) of the cervical spine. The design described in FIGS. 14A and 14B will accommodate this lateral bending and the rotation that occurs in the corresponding region of the spine the device is protecting.

Figure 15A:
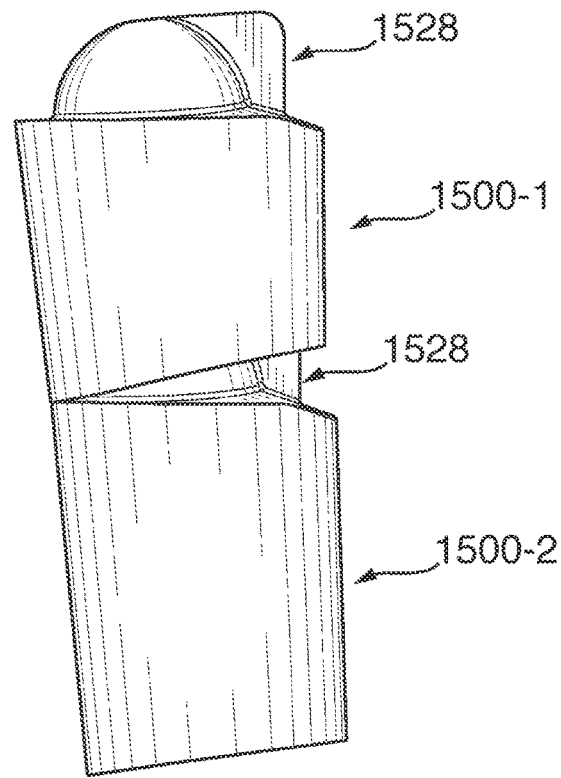
FIGS. 15A and 15B depict two detailed views of an example embodiment of segments with a flat guide protrusion and flat guide indentation, for use as a modular component in the pillar of a head and spine immobilization device.
Figure 15B:
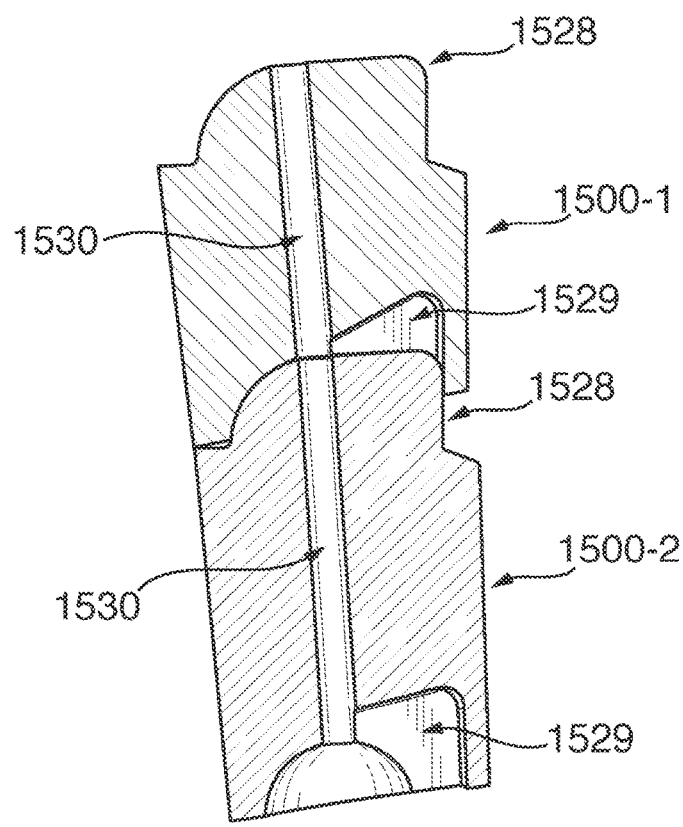

FIGS. 15A and 15B depict two detailed views of an example embodiment of segments 1500-1 and 1500-2, both with a flat guide protrusion 1528 and flat guide indentation 1529, for use as a modular component in the pillar of a head and spine immobilization device, such as depicted in FIGS. 1, 2, 11, and 15. The segments 1500-1 and 1500-2 are generally of the same geometry as shown in FIGS. 13A and 13B, but are shown with the flat guide protrusion 1528 and flat guide indentation 1529. FIG. 15A shows how the segments 1500-1 and 1500-2 interlock within a pillar. FIG. 15B shows a cross-section of the segments 1500-1 and 1500-2, and shows the hollow lumen 1530 running through the longitudinal axis of the segments 1500-1 and 1500-2. FIG. 15B depicts how the flat guide indentation 1529 is deeper than the reciprocal flat guide protrusion 1528. This allows the segments 1500-1 and 1500-2 to rotate in one axis, but provide support in the other axes. This configuration allows the pillar to offer great flexibility for particular applications, such as to allowing a user to freely bend forward and backward within a predetermined range, which will typically be established based on the typical safe range of motion for a user. However, in the event of the pillar flexing outside this predetermined range of motion, the segments 1500-1 and 1500-2 would inhibit the motion, as the flat guide protrusion 1528 reaches the maximum angle allowed within the flat guide indentation 1529, which is shown in more detail in FIGS. 16A and 16B, below. In some embodiments, the segments 1500-1 and 1500-2 act as a dampened endpoint by modifying the tensioning force of the cable when a traumatic event has occurred. For example, after the initial micro- or milliseconds of system activation, the cable running through hollow lumen 1530 can be tensioned first to a sub-maximal force, which still allows some limited motion between the segments. At a later stage of the system activation (possibly only micro- or milliseconds later) the tensioning force in the cable running through the hollow lumen 1530 can be increased to increase the friction between the segments and confer increased rigidity and full or almost full immobilization.

Figure 16A:
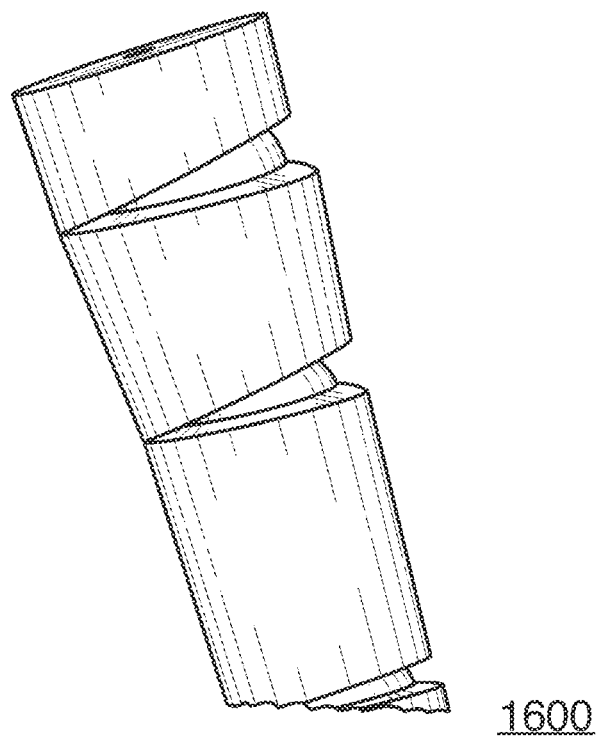
FIGS. 16A and 16B show an example embodiment of a pillar in a two different angles and for use in an immobilization device.
Figure 16B:
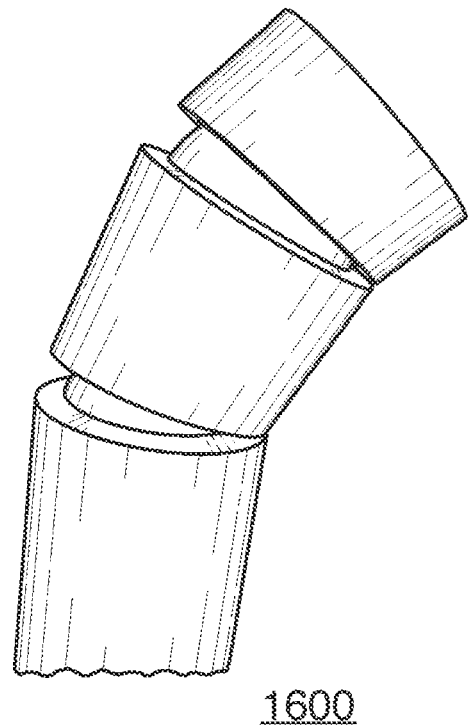

FIGS. 16A and 16B show an example embodiment of a pillar 1600 in a two different angles and for use in an immobilization device. The pillar 1600 can be composed of segments depicted in FIG. 3A, 3B, 16A, 16B, 17A, or 17B or a combination of the different segments depicted. FIG. 16A shows pillar 1600 that is flexed FIG. 16B shows pillar 1600 extended, such as while a user is bending back or is forced backward by an external force. FIG. 16B shows how varying the geometry of the segments used in the pillar can inhibit flexion or extension to a predetermined range, optimally, to a range considered safe for normal motion, and to thereby prevent injuries caused by linear, angular, and/or axial loading. As shown, FIG. 16B shows the pillar 1600 with full extension, with the segments inhibiting further extension in the pillar, and as a result forceful loading, based on the geometry of the segments used in the pillar 1600. In this case, if the user is put into a hazardous situation, such as the user falling onto their anterior head or a blast wave striking the anterior of the user, the pillar 1600 offers support to resist and inhibit further loading, which could cause injury to the spine, nerves and/or brain of the user.

The segments within the pillar 1600 can have a variety of geometric shapes, depending on the application, size of the user or cost. The shape of the segments may be symmetric or asymmetric and be designed in such a way to allow preferential motion (e.g. more flexion and less extension). The material and the geometry will be selected based on the system and component strength necessary to provide the stability required during exposure to non-physiologic forces, such a that caused by explosion or falls from heights. In some embodiments, an articulation between adjacent segments will help maintain orientation of segments relative to one another using a flat guide protrusion and indentation, and block movement of the individual segments relative to one another in specific directions beyond a certain predetermined range. Further, the segments may be asymmetric to confer more rigidity in the activated state and/or have shapes that can create a coupled rotational motion when lateral bending forces are applied. In some example embodiments, each segment will be designed geometrically to afford the appropriate amount of intersegment flexion, extension, rotation, lateral bending and coupled motions. The amount of, or degrees of, intersegment motion when combined with all segments will afford the global range of motion of the protected portion of the spine.

Figure 17:
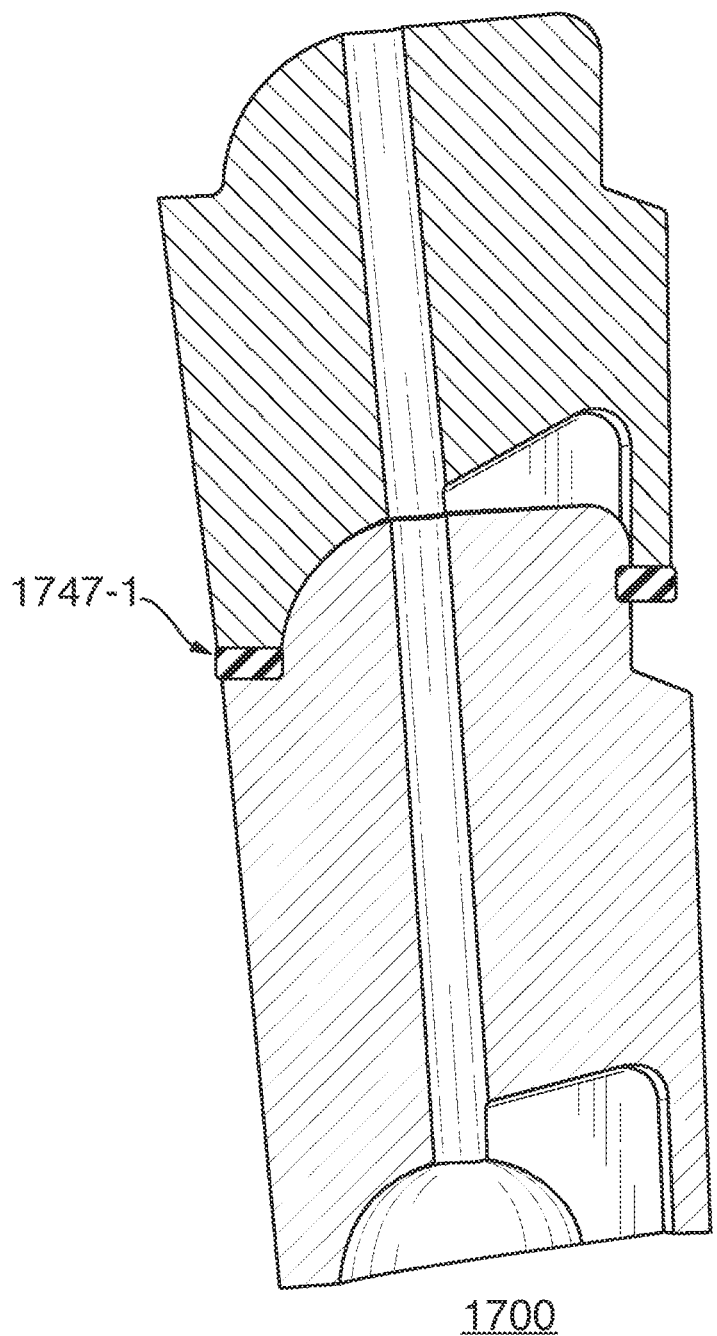
FIG. 17 depicts a detailed view of an example embodiment of segments with dampeners and for use as a modular component in the pillar of a head and spine immobilization device.

FIG. 17 depicts a detailed view of an example embodiment of segments 1700 with dampener 1747 and for use as a modular component in the pillar of a head and spine immobilization device, such as depicted in FIGS. 1, 2, 11, and 15. The segments 1700-1 and 1700-2 are generally of the same geometry as described in FIGS. 15A and 15B but include a dampener 1747 between portions of the segments 1700-1 and 1700-2 that may come in and out of contact through movement of the user or through a sudden traumatic force. As shown, the dampener 1747 buffers segment 1700-1 and segment 1700-2 and prevents direct contact between the lips of segment 1700-1 and segment 1700-2. The dampener 1747 can be of various designs or materials, including rubber or plastic bands, springs, hydraulics, magnetic, electromagnetic, or other mechanical mechanisms. The dampener 1747 can be composed of semi-rigid materials that allow the intrinsic stiffness of the semi-rigid material to vary according the applied force between segments 1700-1 and 1700-2. As such, the dampener can provide a dampened endpoint, where resistance is provided without full or partial activation of the system including segments 1700-1 and 1700-2 through tensioning the cable running through the lumen of the segments 1700-1 and 1700-2. Furthermore, while the dampener 1747 is shown used in conjunction with the segments depicted in FIGS. 15A and 15B, a person of ordinary skill in the art would appreciate that a dampener as describe above could also be used with all of the segments depicted herein, for example, those depicted in FIGS. 3A, 3B, 4, 5A, 5B, 10A, 10B, 100, 13A, 13B, 14A, 14B, 16A, and 16B.

Figure 18A:
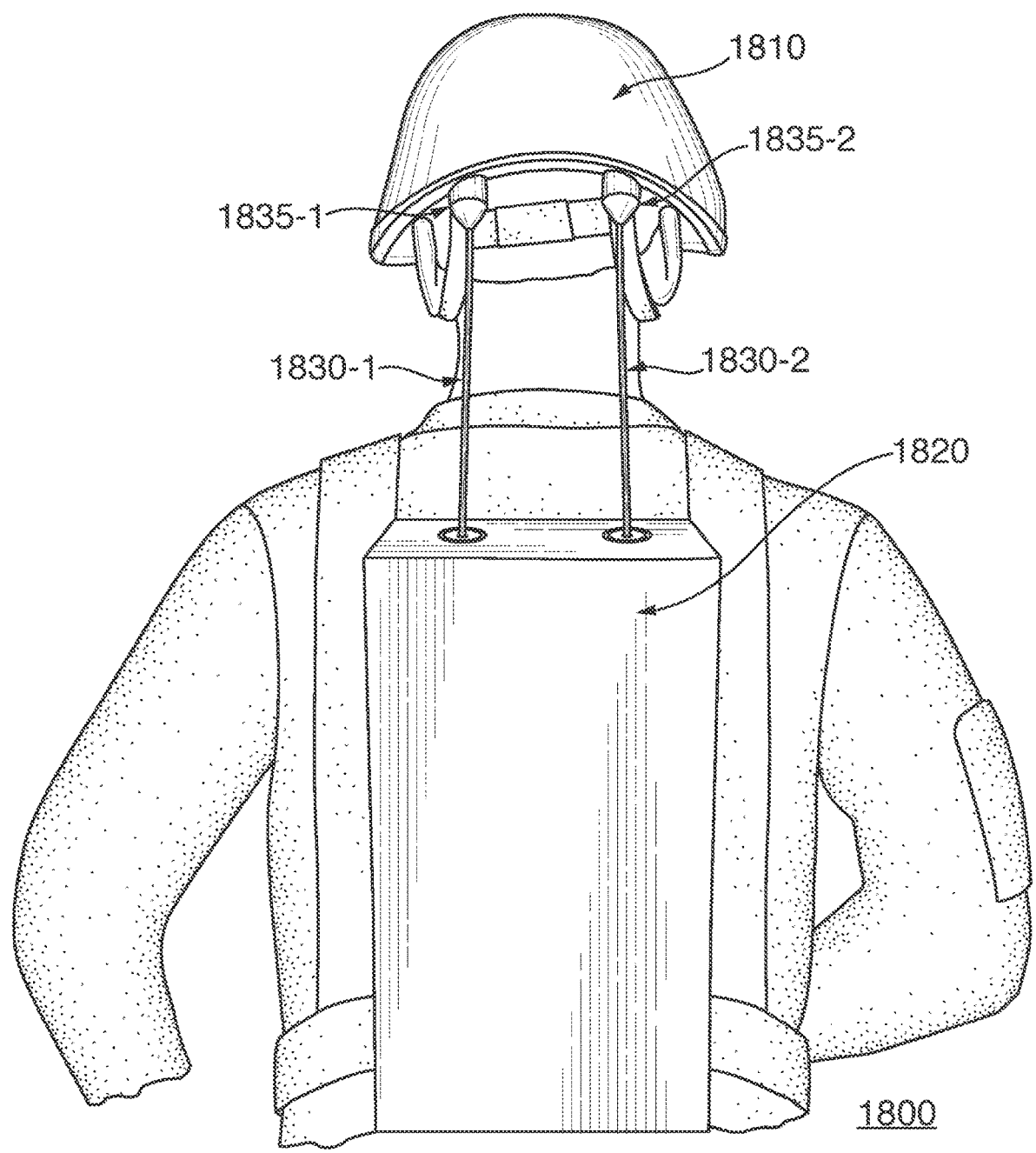
FIGS. 18A and 18B depict an alternative example embodiment of an immobilization device in an activated and inactivated state.

FIG. 18A depicts an example embodiment of an immobilization device 1800 in the inactive state, including a helmet 1810, a vest 1820, cables 1830-1 and 1830-2, and conical receivers 1835-1 and 1835-2. The helmet 1810 is designed to be worn by a user and has as conical receivers 1835-1 and 1835-2 securely attached to the helmet 1810.

The conical receivers 1835-1 and 1835-2 have cables 1830-1 and 1830-2 attached to the helmet and pass through and are anchored in the center of the conical receivers 1835-1 and 1835-2. The cables 1830-1 and 1830-2 traverses inferiorly from the conical receivers 1835-1 and 1835-2 to the housing mechanism in the vest 1820, which is located on the posterior aspect of the user.

Figure 22A:
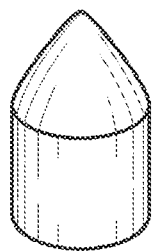
Figure 22B:
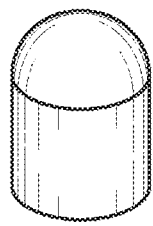
Figure 22C:
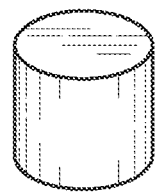

The conical receivers 1835-1 and 1835-2 may be comprised of metal, metal alloy, synthetic, or other durable material. The conical receivers 1835-1 and 1835-2 will have a conical tip through which the respective cables 1830-1 and 1830-2 travel. A portion of the conical receivers 1835-1 and 1835-2 will be cylindrical to afford more rigidity to the system as the tubes dock over the conical receivers 1835-1 and 1835-2. A number of geometries are possible based on the application of the immobilization device, including those that are not conical, and are shown in FIGS. 22A, 22B, and 22C. An example conical receiver with a cylindrical portion is shown in more detail in FIGS. 19A and 19B. The conical receivers 1835-1 and 1835-2 are affixed in a secure manner to the helmet 1810 at an appropriate region of the user to achieve the desired protection.

The conical receivers 1835-1 and 1835-2 are mounted on the posterior aspect of the helmet 1810 to protect the head and upper spine of the user. The conical receivers 1835-1 and 1835-2 are designed such that when the immobilization device is in the inactive state the angular direction of the conical receivers 1835-1 and 1835-2 can change to accommodate normal motion of the user's head and spine. This accommodation by the conical receivers 1835-1 and 1835-2 allows the user unrestricted motion of the head and spine. With activation of the immobilization device 1800, the conical receivers 1835-1 and 1835-2 become unidirectional and fixed. Upon activation, tubes will deploy over the cables 1830-1 and 1830-2, mate over the conical receivers 1835-1 and 1835-2, and by doing so, will lock the conical receivers 1835-1 and 1835-2, and hence, head and neck, in the appropriate position.

Figure 21A:
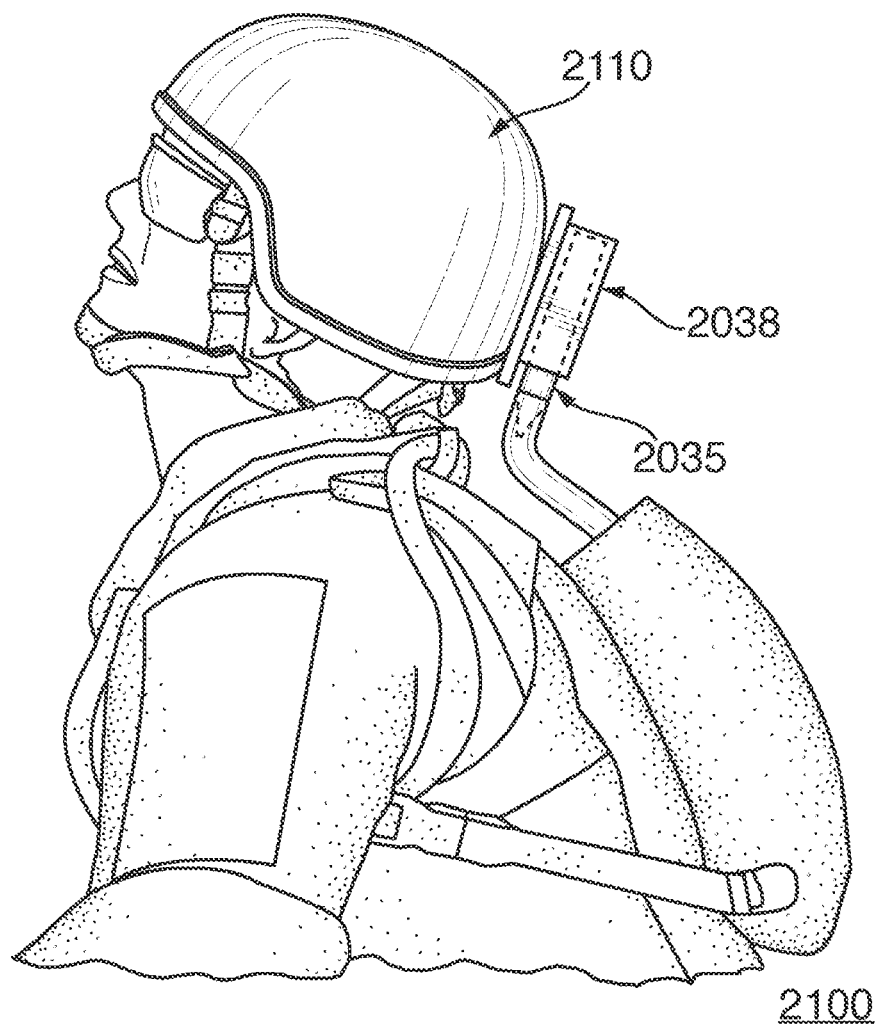
FIGS. 21A and 22B depict an embodiment of an immobilization device with a conical receiver with a telescoping housing attached to the helmet.

In some example embodiments, the conical receivers 1835-1 and 1835-2 attach to the helmet 1810 through a sliding and/or telescoping base, shown in more detail in FIGS. 21A and 22B, to accommodate for the movement of the user through the angular direction of the conical receivers 1835-1 and 1835-2. This sliding and/or telescoping base for the conical receivers 1835-1 and 1835-2 are freely sliding and/or telescoping when the immobilization device 1800 is in the inactivated state, in order to allow a full range of motion for the user. When the immobilization device 1800 is activated, the sliding and/or telescoping conical receivers 1835-1 and 1835-2 are locked in place, in order to confer to the rigidity of the system. In some example embodiments, the accommodation by the conical receivers 1835-1 and 1835-2 can also be achieved by having them attached to a ball and socket joint embedded in the helmet 1810.

The vest 1820 has a housing apparatus built in on the anterior, lateral and/or posterior aspect. The housing apparatus contains a rigid tube for each of the cables 1830-1 and 1830-2, as well as the mechanism to deploy the rigid tubes during system activation and retract the rigid tubes during system deactivation. During activation, the rigid tubes quickly deploy over the cables 1830-1 and 1830-2 and mate with the conical receivers 1835-1 and 1835-2 to confer the specified rigidity to the system. The movement of the rigid tubes into their activated state can be performed electrically, magnetically, mechanically (e.g. spring system), hydraulically, and/or by using compressed gas, and/or pyrotechnic charge(s).

The immobilization device 1800 can include a number of mechanisms in the housing apparatus to sense the position of the head and spine and to trigger activation of the immobilization device. The immobilization device 1800 activates the rigid tubes at an angle and force that is appropriate for the position of the head and spine. This "proprioceptive" capacity of the immobilization device 1800 avoids recoil of the head or spine when the immobilization device 1800 is activated. The proprioceptive mechanism causes the cables 1830-1 and 1830-2 to move in the direction opposite of their respective rigid tube motion and takes up slack in the cables 1830-1 and 1830-2 when the user moves their head. For example, if the user's neck is extended (looking up) this causes slack in the cables 1830-1 and 1830-2 as the conical receivers 1835-1 and 1835-2 move closer to the vest 1820. If the immobilization device 1800 is activated in this position, a proprioceptive mechanism will tension the cables 1830-1 and 1830-2 as the rigid tubes move in the opposite direction toward the conical receivers 1835-1 and 1835-2. In some example embodiments, this is accomplished by having the terminal end of the cables 1830-1 and 1830-2 embedded in a piston of a solid material within the housing apparatus in the vest 1820. The immobilization device can use sensors on the piston or a gyroscopic device to detect the position of the user's head. Upon activation of the immobilization device, a driver, or piston into which the lower terminal ends of the cables 1830-1 and 1830-2 are anchored would travel opposite the rigid tubes to counteract the force of the rigid tubes moving in the opposite direction. This would prevent unwanted recoil of the user's head and neck. In doing so, the user's body part would be locked in the position at the time of activation. In some example embodiments, to allow full movement of the head and neck, the vest 1820 may also include a spooling mechanism, allowing some extension or retraction of the cables 1830-1 and 1830-2 based on the positioning of the user's head. In this example, a sensor on the spooling mechanism to detect the position of the head of the user.

In some example embodiments, the housing apparatus swivels and/or rotates to accommodate deployment or retraction of the rigid tubes with the user in various positions. For example, if a soldier is exposed to a dangerous explosive blast force when his head is rotated, the housing apparatus will swivel and/or rotate to an appropriate degree to allow an appropriate path of deployment and/or retraction of the rigid tubes.

In some example embodiments, a housing apparatus is anchored to the vest 1820 to achieve the necessary stability of the immobilization device 1800 during the active (rigid) and inactive (flexible) states. The vest 1820 maybe designed specifically to be a component in the immobilization device 1800, or is an existing tactical or military style vest or garment and/or a new specially designed tactical or military style vest. For military applications, the outer material of the housing apparatus and anchoring material may contribute to the body armor.

FIG. 18A depicts the immobilization device 1800 in the inactive stated and the user has full, physiologic motion of the head and neck. Inside the vest 1820 includes rigid tubes (not shown) for each of the cables 1830-1 and 1830-2, with the cables 1830-1 and 1830-2 running through the interior of the rigid tubes. The immobilization device 1800 can be activated to extend rigid tubes to confer the desired rigidity to the system. However, when the immobilization device 1800 is inactive, the rigid tubes are located in a specialized housing located in the vest 1820. Upon activation, a mechanism in the housing will displace the rigid tubes over the cable or wire in the direction of the conical receivers 1835-1 and 1835-2. Due to the geometry of the conical receivers 1835-1 and 1835-2 and the design of the housing mechanism in the vest 1820, after activation, the rigid tubes will support the helmet 1810 by connecting to the vest 1820. The deployment of the rigid tubes to the helmet 1810 and vest 1820 prevents the harmful motion of the spine and head. The immobilization device 1800 can be deactivated, where the rigid tubes are automatically or manually retracted back into their inactive position within the housing mechanism.

In some example embodiments, the immobilization device 1800 also protects the lower spine. In these embodiments, the immobilization device includes a cable or wire that passes from the vest 1820 inferiorly to similar conical receivers that are part of a pelvic harness. In this embodiment, when the immobilization device is activated, rigid tubes would also extend inferiorly to the pelvic harness and mate with the conical receivers on the pelvic harness. In this example embodiment, the user will have full, physiologic motion of the lower back. The location of the conical receivers and tubes need not be necessarily on the posterior aspect of the user based on the anticipated application. The conical receivers may also be anterior, on the sides and/or posteriorly.

In some example embodiments the immobilization device 1800 can be activated by sensors located either in the helmet of the user, on another part of the user, or in another location, such as the vehicle the user is traveling. The sensors may be activated by acceleration, position, heat, light, pressure, or other stimuli. The transmission of data from the sensor to the activation mechanism within the vest 1810 can be done with radiofrequency, wire, hydraulics or other. The immobilization device 1800 may include a processor and memory to process the stimuli from its various sensors and apply the correct response based on the current conditions and the parameters set for the immobilization device 1800. For example, the immobilization device 1800 may activate under more or less extreme circumstances given the user (e.g. older, younger, frail, injured), the application (e.g. soldier, pilot, sport), or the force of the threat incurred (e.g. explosion, collision, other impact).

In some example embodiments, the housing apparatus in the vest 1810 has an actuator responsible for the electronic sensor signal receipt and transmission, and deployment and retraction of the rigid tubes. A person of ordinary skill in the art would understand that a number of mechanical designs are possible to achieve the desired action of the actuator.

Figure 18B:
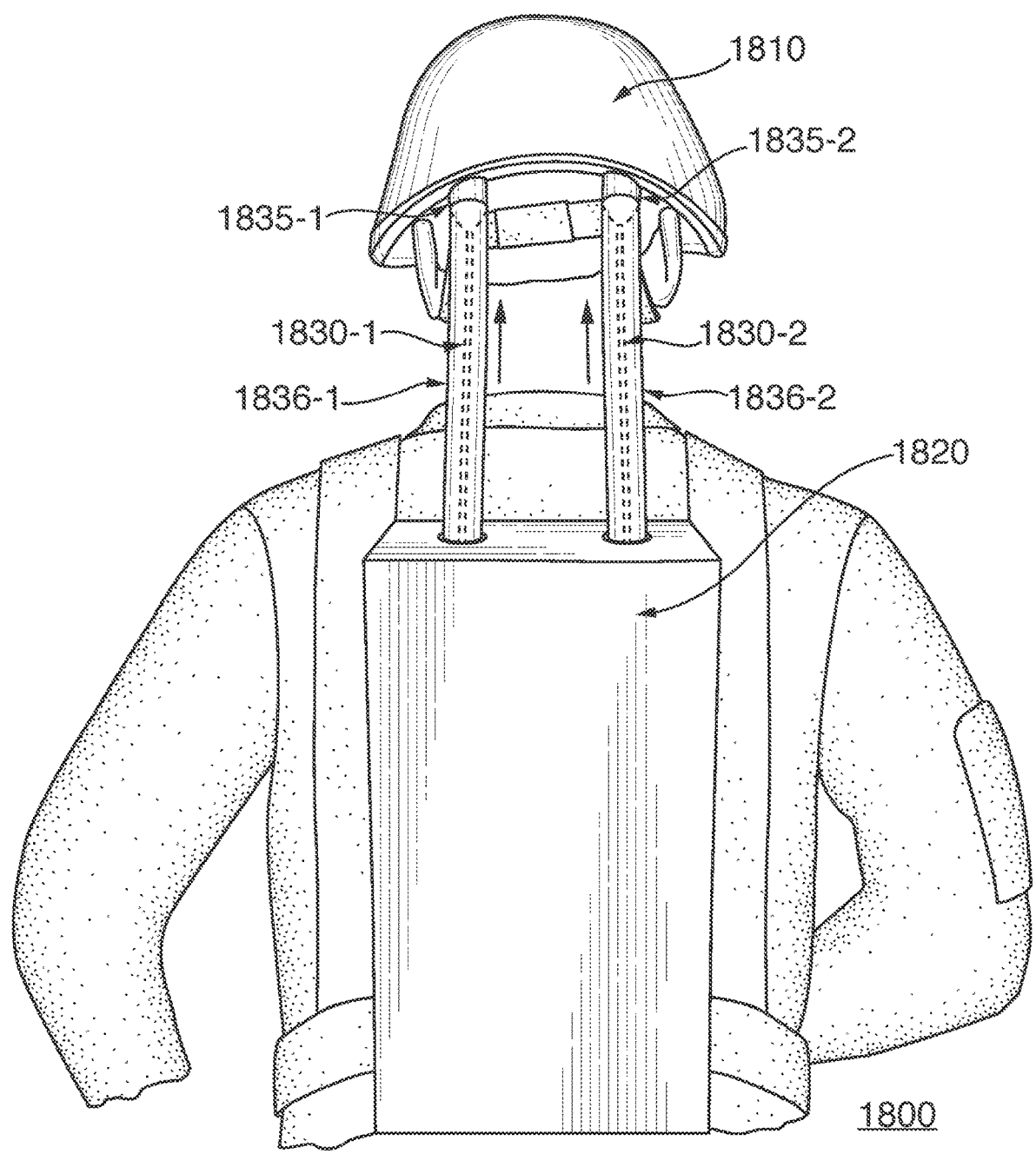

FIG. 18B depicts an example embodiment of an immobilization device 1800 in the activated state and including a helmet 1810, a vest 1820, cables 1830-1 and 1830-2, conical receivers 1835-1 and 1835-2, and rigid tubes 1836-1 and 1836-2. The immobilization device 1800 depicted in FIG. 18B is the same as in FIG. 18A, but is shown in the activated stated with the rigid tubes 1836-1 and 1836-2 shown. The rigid tubes 1836-1 and 1836-2 are shown to be mated with the conical receivers 1835-1 and 1835-2. This confers rigidity to the immobilization device 1800 while it is activated.

In some example embodiments, the rigid tubes 1836-1 and 1836-2 will be made of metal, metal alloy, synthetic, or another durable, rigid material. The rigid tubes 1836-1 and 1836-2 are shown as solid tubes. However, the rigid tubes 1836-1 and 1836-2 can be several segmented tubes that extend and lock in place, instead of one continuous rigid material. Furthermore, while the tubes are shown with a circular cross-section, other cross-sections can be used, such as oval, square, rectangle, hexagon, or octagon.

In some example embodiments, the rigid tubes 1836-1 and 1836-2 retract back into the housing mechanism in the vest 1820, and hence deactivate the system. Deactivation of the immobilization device 1800 can occur automatically after an impact, or manually, depending on the desired application of this invention. There are various designs that can confer the automatic retraction, including hydraulic, mechanical (i.e., a spring or band), electromagnetic, pyrotechnic, compressed gas, or a combination of these. The timing and speed of automatic retraction can be programmed into microprocessor or circuitry and design of the device. For example, if the immobilization device 1800 is intended to be used in situations of combat it may be ideal for the user to be immediately protected by this device when exposed to a blast, but then seconds later be able to return to full function and motion after the harmful stimuli is no longer present. In the case of manual tube retraction, there are several device designs to achieve this, and can include the use of a crank or manually asserting pressure on the rigid tube by hand or foot.

Figure 19A:
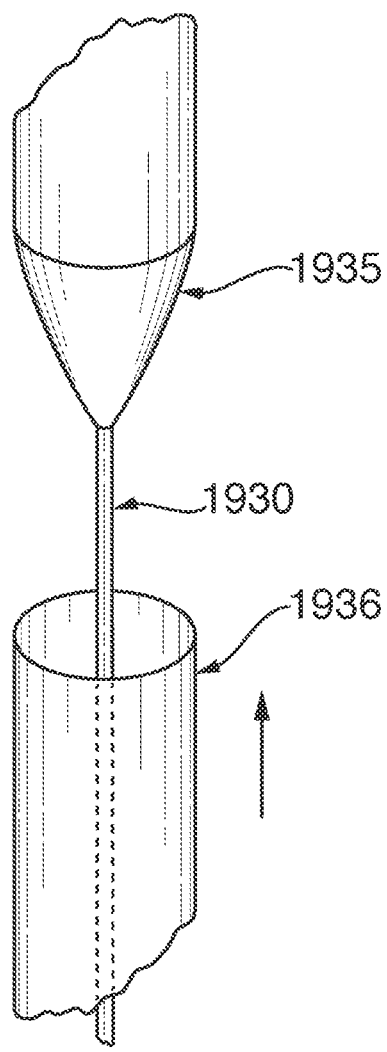
FIGS. 19A and 19B depict detailed views of an example embodiment of a conical received and rigid tube in the process of activation and while activated.

FIG. 19A depicts a cable 1930, conical receiver 1935, and rigid tube 1936. The rigid tube 1936 is shown extending toward the conical receiver 1935 as it is in the process of activation. The rigid tube is shown traveling guided by the cable 1930. The conical receiver 1935 is shown with a conical portion extending tapering to a tip with the cable 1930 extending. The conical receiver 1935 is also shown with a cylindrical portion.

Figure 19B:
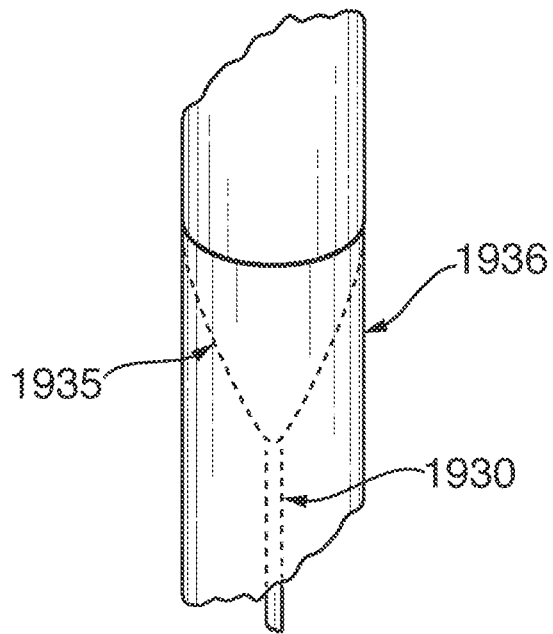

FIG. 19B depicts a cable 1930, conical receiver 1935, and rigid tube 1936. FIG. 19B shows the same components as FIG. 19A, but with the completion of the activation, and the rigid tube 1936 in place over the conical receiver 1935.

Figure 20:
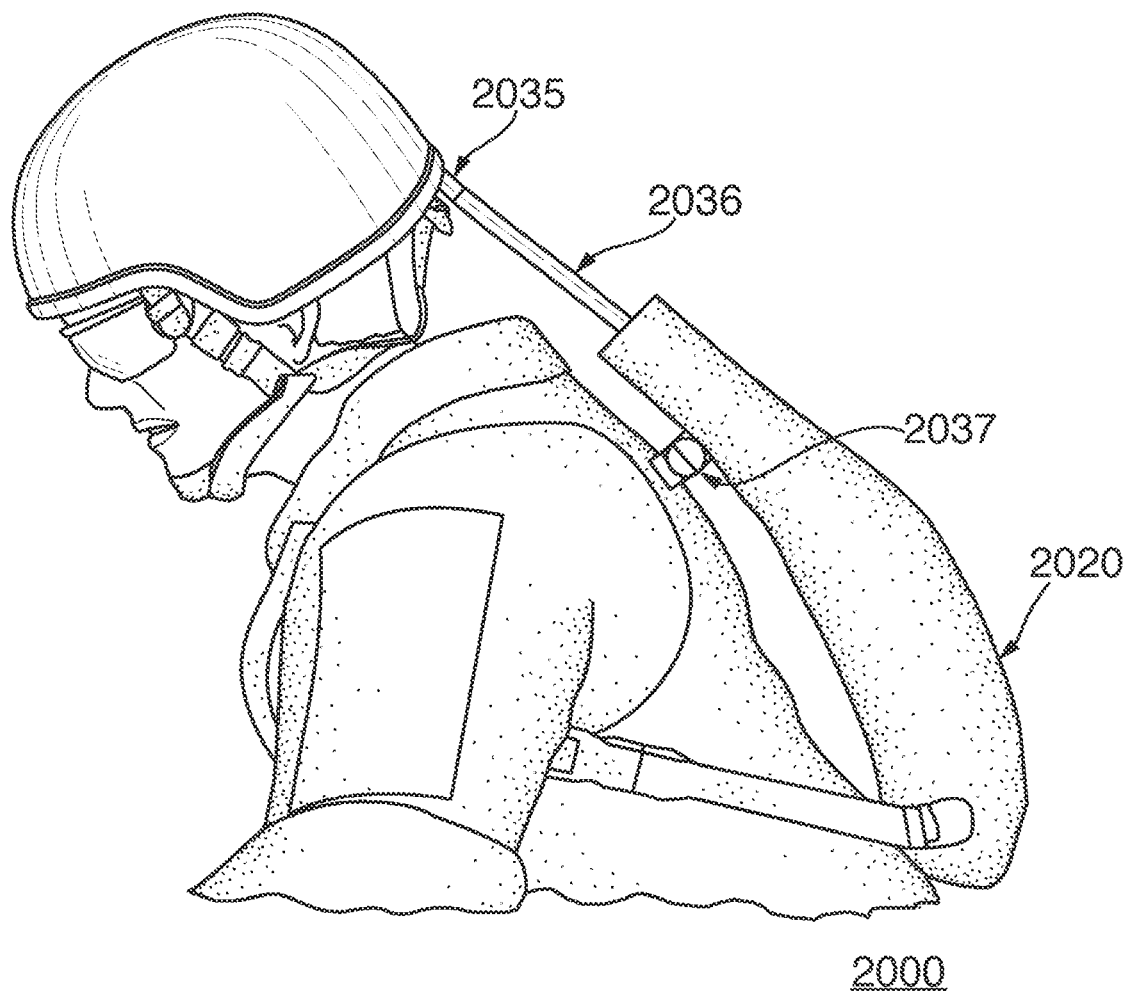
FIG. 20 depicts an example embodiment of an immobilization device with a conical receiver, rigid tube and swiveling mechanism.

FIG. 20 depicts an example embodiment of an immobilization device 2000 with a conical receiver 2035, rigid tube 2036 and swiveling mechanism 2037. Immobilization device 2000 includes a system with a conical receiver 2035 and rigid tube 2036, as described in reference to FIGS. 18A and 18B. In this embodiment, a swiveling mechanism 2037 is included with the vest 2020. The swiveling mechanism 2037 is a swivel that allows for increased movement of the user in the sagittal and coronal planes when the immobilization device 2000 during activation. After activation, this swivel will be also locked to provide necessary stability of the protected body part. In some example embodiments, the swiveling mechanism 2037 is ball and socket hardware that allows the swiveling mechanism 2037 to move in multiple planes. In other example embodiments, the swiveling mechanism 2037 is a hinge that limits movement to a single plane. The immobilization device 2000 is the same as the immobilization device depicted in FIGS. 18A and 18B with rigid tubes and conical receivers.

Figure 21B:
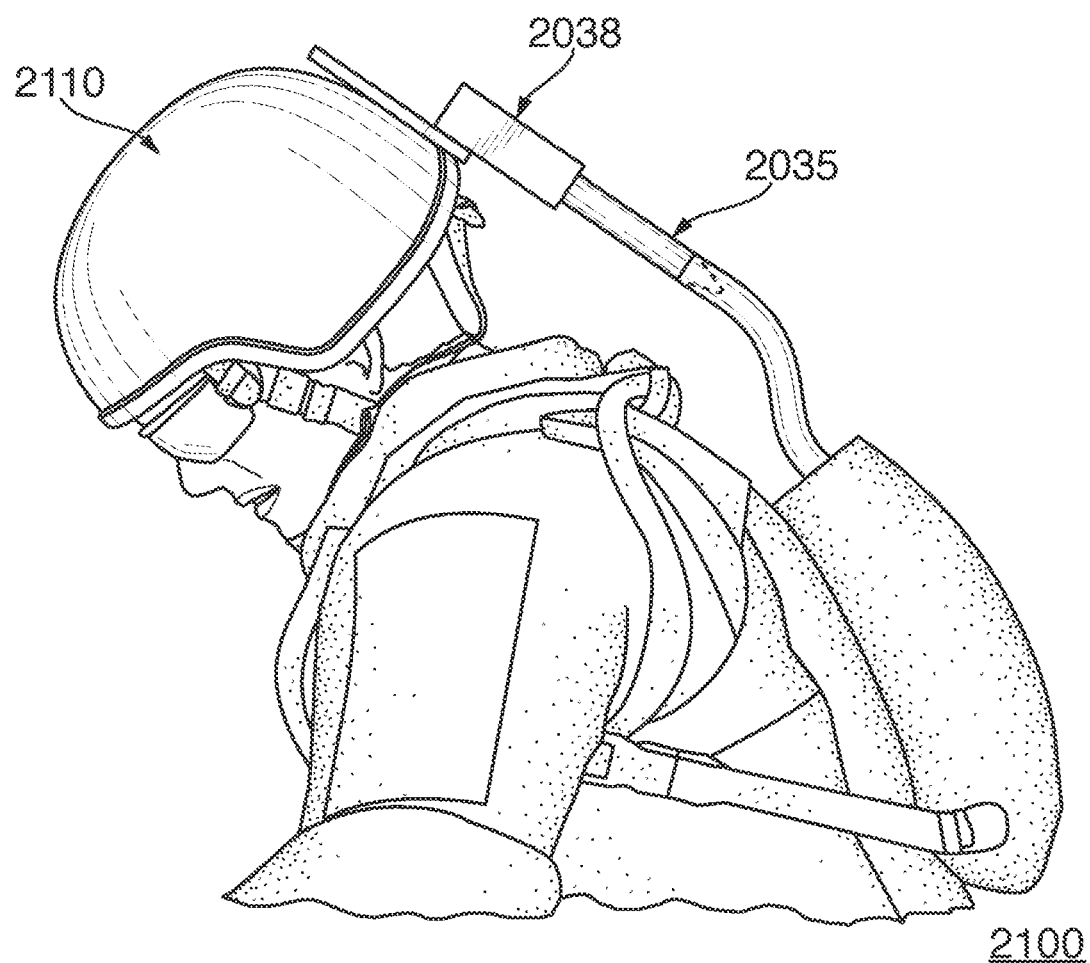

FIGS. 21A and 22B depict an embodiment of an immobilization device 2100 with a conical receiver 2035 with a telescoping housing 2038 attached to the helmet 2110. Immobilization device 2000 includes a system with a conical receiver 2035 and rigid tube (not shown), as described in reference to FIGS. 18A, 18B and 20. FIGS. 21A and 21B show a telescoping housing being used, which, in some embodiments, will reduce potential hindrance of head movement of the user while using immobilization device 2100. For example, as shown in FIG. 21A when a user tilts their head backwards, the conical receiver 2035 will telescope into the telescoping housing 2038. However, as shown in FIG. 21B, when a user tilts their head forwards the conical receiver 2035 will telescope out of the telescoping housing 2038.

FIGS. 22A, 22B, 22C depict example embodiments of conical receivers with different geometries. In some example embodiments, the conical receiver has a similar cross-section to the corresponding rigid tube. For example, a rigid tube with a circular cross-section would have a conical receiver with a circular cross-section. However, as discussed above in reference to FIG. 18B, different cross-sections, such as oval, square, rectangle, hexagon, octagon, etc. can be used. The conical receivers depicted in FIGS. 22A, 22B, and 22C may be comprised of metal, metal alloy, synthetic, or other durable material. In some example embodiments, the conical receiver will also be a rigid material and in others a flexible material such as rubber or plastic is preferable. FIG. 22A depicts a conical receiver as seem in FIGS. 18A, 18B, 19A, 19B, 20, 21A, and 21B, with a spherical base, leading to a conical portion leading to pointed tip. FIG. 22B depicts a conical receiver with a rounded end, instead of a pointed tip. FIG. 22C depicts a conical receiver with a flat surface, instead of a pointed tip.

Figure 23A:
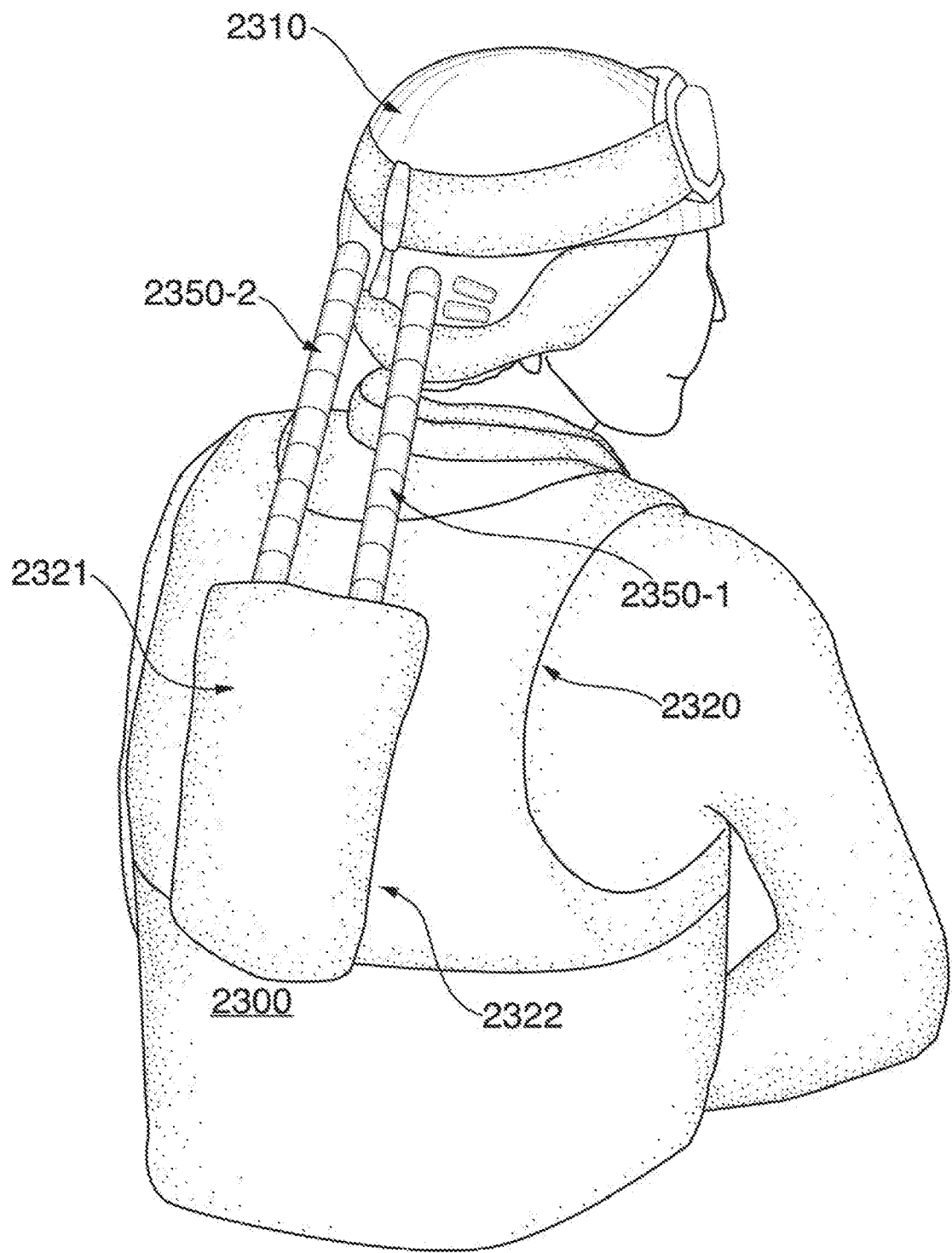
FIGS. 23A and 23B depict two views of an immobilization device designed for use during extreme sports or aviation.
Figure 23B:
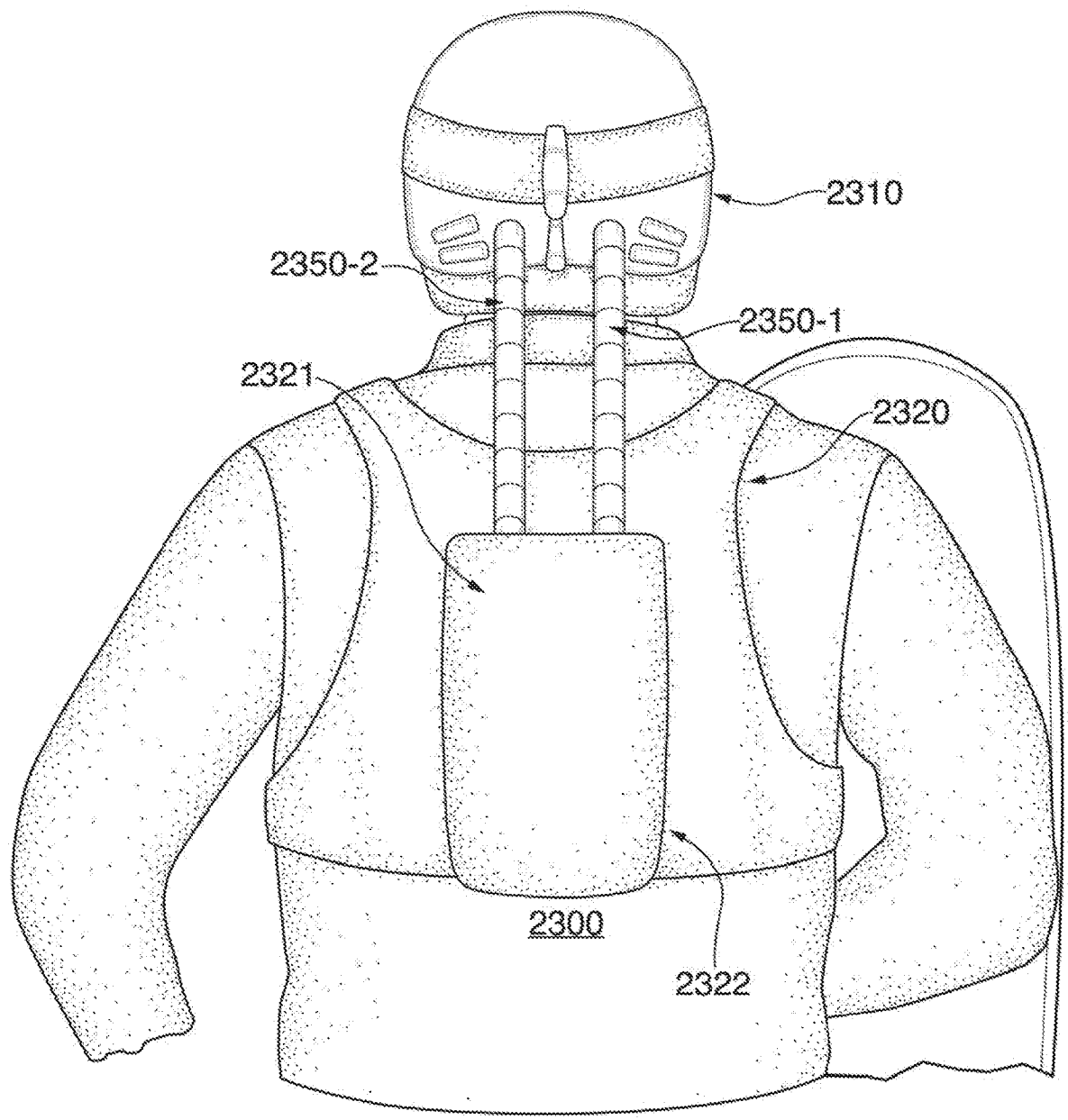

FIGS. 23A and 23B depict an alternative example embodiments of an immobilization device 2300 designed for use for extreme sporting (e.g. off-trail skiing and snowboarding, mountain biking, motocross, riding four wheel all-terrain vehicle riding, etc.) or for airplane pilots (in particular military and jet pilots) with a helmet 2310, a vest 2320, and pillars 2350-1 and 2350-2. The immobilization device 2300 is designed to act as an exoskeleton or external brace by channeling the forces to the device and away from the person's body. In this embodiment, the device does not include a sensor mechanism or an activation mechanism in the vest housing 2320 as previously described. In this embodiment protection of the spine is achieved by preventing the non-physiologic extremes of motion beyond which soft tissue and boney injury are known to occur. An example of one such scenario is a downhill skier striking a tree. Rather, this exoskeleton device prevents harmful extremes of head and neck motion by virtue of the cable, and the materials and the geometry of the individual segments within the pillars 2350-1 and 2350-2. This immobilizations device 2300 will prevent brain and spinal injury that can occur during extreme sports and during flight maneuvers typical of military aviation. The immobilization device 2300 is preferably constructed of lightweight durable materials, such as metal, ceramic, plastic or carbon fiber. Furthermore, it is preferably small and unobtrusive so that it does not interfere with the user range of motion while participating in extreme sports.

One end of the pillars used in the immobilization device 2300 is securely connected to the posterior aspect of the helmet 2310, while the other end is connected to the housing apparatus in the vest 2320. The vest 2320 can include a housing apparatus 2321 portion containing the anchor and translation mechanism for the pillars 2350-1 and 2350-2 to provide support and allow physiologic motion, respectively. For example, if an object strikes the fact or head of a user of immobilization device 2300 while they are using the immobilization device 2300 (e.g. while participating in extreme sports) the pillars 2350-1 and 2350-2 will prevent extension of the head and neck beyond the normal limits. The pillars 2350-1 and 2350-2 prevent the extension of the head and neck based on the geometry of the segments included in the pillars 2350-1 and 2350-2. The housing apparatus 2321 in posterior aspect of the vest 2320 is designed to be the lower terminal connection of the pillars 2350-1 and 2350-2 for head and upper spine protection, or the upper terminal connection for lower spine and sacrum protection. The housing apparatus 2321 allows some translation, telescoping, and/or rotation of the pillars to accommodate necessary motion pillar motion during the normal ranges of bodily motion. For example, during normal neck forward flexion, the housing apparatus will allow the pillar system to lengthen in a controlled manner. The housing apparatus 2321 is attached to a flexible jacket 2322 that is worn by the user of the device.

Figure 10C:
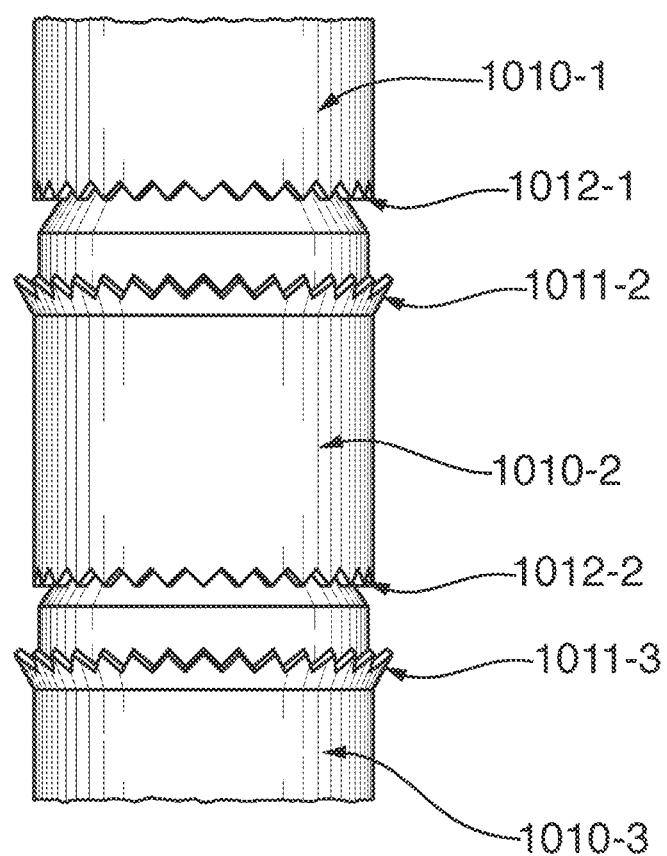

During potentially harmful situations, such as during an accident or extreme acceleration, the immobilization device 2300 confers stabilization to the user through the geometry of the segments within the pillars 2350-1 and 235002, which prevent the extension of the head and neck beyond normal limits. The segments can be formed as described in FIGS. 10A-10C. In one example embodiment, the segments are formed as in FIG. 10A, and include peripheral protections on one or more of the segments in the pillars 2350-1 and 2350-2, which prevent bending of the pillars beyond a predetermined angle consistent with the normal range of motion of a user. In another example embodiment, the segments are formed as in FIG. 100, and include dentate peripheral projections. These dentate peripheral projections prevent both the bending and rotational movement of the pillars 2350-1 and 2350-2 to prevent bending and rotation outside the normal range of motion of a user.

In reading the above description, persons skilled in the art will realize that there are apparent variations that can be applied to the methods and systems described. In the foregoing specification, the invention has been described with reference to specific exemplary embodiments thereof. It will, however, be evident that various modifications and changes may be made to the specific exemplary embodiments without departing from the broader spirit and scope of the invention as set forth in the appended claims. Accordingly, the specification and drawings are to be regarded as illustrative rather than restrictive. Furthermore, a person of ordinary skill in the art would understand that aspects related to a specific embodiment can also be applied to other disclosed embodiments.

What is claimed is:

1. A rapid deployment immobilization system comprising:
    a helmet including a first receiver from which a first flexible cable extends and a second receiver from which a second flexible cable extends;
    a vest including a first rigid hollow elongated tube with the first cable running through an interior of the first rigid hollow elongated tube and affixed to the vest and a second rigid hollow elongated tube with the second cable running through an interior of the second rigid hollow elongated tube and affixed to the vest; and
    a rapid deployment mechanism, wherein the rapid deployment mechanism includes a gyroscope, accelerometer, manometer, or a combination thereof, and an actuator, wherein the actuator type is a gear locking mechanism including a piston that rotates two gears;
    wherein the rapid deployment mechanism has an inactive state and an activated state;
    wherein in the inactive state, the first and second rigid hollow elongated tubes are located entirely within the vest and do not immobilize the rapid deployment immobilization system relative to the helmet and the vest; and
    wherein when the rapid deployment mechanism transitions to the activated state, the actuator operates to extend the first rigid hollow elongated tube out of the vest and guided by the first cable onto the first receiver in the helmet and to extend the second rigid hollow elongated tube out of the vest and guided by the second cable onto the second receiver in the helmet, thereby rapidly immobilizing the rapid deployment immobilization system relative to the helmet and the vest.

2. A rapid deployment immobilization device as in claim 1, wherein the first and second receivers are cylindrical.

3. A rapid deployment immobilization device as in claim 1, wherein the first and second receivers are conical.

4. A rapid deployment immobilization device as in claim 1, wherein the helmet includes a telescoping base operable to telescope the first and second receivers.

5. A rapid deployment immobilization device as in claim 1, wherein the rapid deployment mechanism includes a proprioceptive mechanism that tensions the first and second cables when the rapid deployment immobilization is transitioning from the inactive to the active state and thereby taking up slack in the first and second cables.

6. A rapid deployment immobilization device as in claim 1, wherein the rapid deployment immobilization system includes a processor and memory to process stimuli from the rapid deployment mechanism and determine the optimal response from the rapid deployment mechanism.

7. A rapid deployment immobilization device as in claim 1, wherein the first and second rigid elongated hollow tubes are metal.

* * * * *